United States Patent
Krayer et al.

(10) Patent No.: US 10,672,251 B1
(45) Date of Patent: Jun. 2, 2020

(54) CONTEXTUAL ASSESSMENT OF CURRENT CONDITIONS

(71) Applicant: C/HCA, Inc., Nashville, TN (US)

(72) Inventors: Christian Krayer, Nolensville, TN (US); William Michael Gregg, Nashville, TN (US); Thomas Andrew Doyle, Franklin, TN (US); Paul Brient, Wayland, MA (US); Jim Najib Jirjis, Nashville, TN (US); Karl Bradley Kehler, Nashville, TN (US); Jonathan Perlin, Nashville, TN (US); Paul Martin Paslick, Nashville, TN (US); Edmund Jackson, Nashville, TN (US); Sarah Hume Buta, Arlington, MA (US); Erin S. Jospe, Newton, MA (US); Umesh P. Phirke, Newton, MA (US)

(73) Assignee: C/HCA, Inc., Nashville, TN (US)

( * ) Notice: Subject to any disclaimer, the term of this patent is extended or adjusted under 35 U.S.C. 154(b) by 0 days.

(21) Appl. No.: 16/358,282

(22) Filed: Mar. 19, 2019

Related U.S. Application Data

(63) Continuation-in-part of application No. 15/902,897, filed on Feb. 22, 2018, now Pat. No. 10,311,701, (Continued)

(51) Int. Cl.
*G08B 21/18* (2006.01)
*G06F 11/30* (2006.01)

(52) U.S. Cl.
CPC ........ *G08B 21/182* (2013.01); *G06F 11/3027* (2013.01)

(58) Field of Classification Search
CPC ..... G06F 19/30; G08B 21/02; G08B 21/0202; G08B 21/0446; G08B 21/0453; G08B 21/22
(Continued)

(56) References Cited

U.S. PATENT DOCUMENTS 6,629,937 B2 * 10/2003 Watrous ............... A61B 7/00
128/920
7,630,986 B1 12/2009 Herz et al.
(Continued)

OTHER PUBLICATIONS

Non-Final Office Action dated Jan. 24, 2019 in related U.S. Appl. No. 15/902,897, 9 pgs.
(Continued)

*Primary Examiner* — Omar Casillashernandez
(74) *Attorney, Agent, or Firm* — Kilpatrick Townsend & Stockton, LLP

(57) ABSTRACT

In some examples, systems, methods, and devices are described that generate contextual suggestions for patients. Generation of the contextual suggestions is triggered by certain events performed by a medical professional with respect to a patient (e.g., updating a patient record). The contextual suggestions are related to addressing health conditions of the patient and represent tasks or considerations which the medical professional should be made aware. The contextual suggestions are generated in a way that is considerate of patient context, medical professional context, and contexts of similar patients. The contextual suggestions can be presented to the medical professional for selection and execution.

15 Claims, 21 Drawing Sheets

Related U.S. Application Data which is a continuation of application No. 15/684,747, filed on Aug. 23, 2017, now Pat. No. 9,905,112, which is a continuation-in-part of application No. 15/357,745, filed on Nov. 21, 2016, now Pat. No. 9,779,611, which is a continuation-in-part of application No. 15/156,503, filed on May 17, 2016, and a continuation-in-part of application No. 14/967,027, filed on Dec. 11, 2015, application No. 16/358,282, which is a continuation-in-part of application No. 15/479,011, filed on Apr. 4, 2017, now Pat. No. 10,296,187.

(60) Provisional application No. 62/317,844, filed on Apr. 4, 2016, provisional application No. 62/163,220, filed on May 18, 2015, provisional application No. 62/095,598, filed on Dec. 22, 2014.

(58) Field of Classification Search
USPC ........................................................ 340/573.1
See application file for complete search history.

(56) References Cited

U.S. PATENT DOCUMENTS

| | | | | |
|---|---|---|---|---|
| 7,769,600 | B2* | 8/2010 | Iliff | G06F 19/3418 705/2 |
| 8,094,009 | B2* | 1/2012 | Allen | A61B 5/01 340/539.11 |
| 8,271,471 | B1 | 9/2012 | Kamvar | |
| 9,060,683 | B2* | 6/2015 | Tran | A61B 5/0022 |
| 9,081,879 | B2* | 7/2015 | Iliff | G06Q 50/22 |
| 9,269,116 | B2* | 2/2016 | Bulat | A61B 5/0002 |
| 9,524,569 | B2 | 12/2016 | Moore | |
| 9,779,611 | B1 | 10/2017 | Krayer et al. | |
| 9,905,112 | B1 | 2/2018 | Krayer et al. | |
| 2001/0042119 | A1* | 11/2001 | Urano | H04L 43/00 709/223 |
| 2004/0172222 | A1* | 9/2004 | Simpson | G06F 19/3418 702/189 |
| 2005/0075970 | A1* | 4/2005 | Doyle | G06Q 10/06 705/38 |
| 2005/0288965 | A1* | 12/2005 | Van Eaton | G06Q 50/22 705/2 |
| 2006/0111941 | A1* | 5/2006 | Blom | G06Q 10/06 705/2 |
| 2006/0241978 | A1* | 10/2006 | Yoshii | G06Q 50/24 705/3 |
| 2007/0094046 | A1 | 4/2007 | Cobbs | |
| 2007/0185390 | A1* | 8/2007 | Perkins | A61B 5/0002 600/300 |
| 2007/0250345 | A1* | 10/2007 | Walker | A61B 5/4806 705/2 |
| 2008/0091464 | A1 | 4/2008 | Lipscher | |
| 2008/0270189 | A1* | 10/2008 | Howard | G06Q 10/10 705/3 |
| 2009/0125334 | A1* | 5/2009 | Krishnan | G06F 19/3481 705/3 |
| 2010/0094649 | A1* | 4/2010 | White | G06F 19/324 705/2 |
| 2011/0046979 | A1* | 2/2011 | Tulipano | G06F 19/325 705/2 |
| 2012/0101847 | A1 | 4/2012 | Johnson | |
| 2012/0109683 | A1 | 5/2012 | Ebadollahi et al. | |
| 2012/0117476 | A1 | 5/2012 | Siegrist | |
| 2012/0130734 | A1* | 5/2012 | White | G06Q 50/22 705/2 |
| 2012/0224057 | A1* | 9/2012 | Gill | G06F 21/55 348/143 |
| 2014/0067418 | A1* | 3/2014 | Hyzy | G06F 19/00 705/3 |
| 2014/0188895 | A1* | 7/2014 | Wang | G06F 16/335 707/748 |
| 2014/0316813 | A1* | 10/2014 | Bauer | G16H 10/60 705/3 |
| 2014/0357312 | A1 | 12/2014 | Davis et al. | |
| 2015/0100943 | A1 | 4/2015 | Gabel et al. | |
| 2015/0193583 | A1 | 7/2015 | McNair | |
| 2016/0034986 | A1* | 2/2016 | Ortiz | G16H 10/60 705/3 |
| 2016/0110502 | A1* | 4/2016 | Bronson | G06Q 50/01 705/3 |
| 2016/0321430 | A1* | 11/2016 | Eckman | G06T 11/206 |
| 2017/0116373 | A1 | 4/2017 | Ginsburg | |
| 2017/0293988 | A1* | 10/2017 | Goyal | G06Q 10/0631 |

OTHER PUBLICATIONS

Notice of Allowance dated Jan. 24, 2019 in related U.S. Appl. No. 15/902,897, 9 pgs.
Notice of Allowance dated May 24, 2017 in related U.S. Appl. No. 15/357,745, all pages.
Notice of Allowance dated Oct. 19, 2017 in related U.S. Appl. No. 15/684,747, 17 pgs.
Non-Final Office Action dated Feb. 9, 2017 in related U.S. Appl. No. 15/357,745, 20 pgs.
Non-Final Office Action dated Mar. 18, 2019 in related U.S. Appl. No. 15/156,503, 39 pgs.
Non-Final Office Action dated Jul. 12, 2018 in related U.S. Appl. No. 14/967,027, 15 pgs.
Non-Final Office action dated Jan. 25, 2019 in related U.S. Appl. No. 14/967,027, 14 pgs.
Final Office Action dated Aug. 8, 2019 in U.S. Appl. No. 14/967,027, 16 pgs.

* cited by examiner

CONTEXTUAL ASSESSMENT OF CURRENT CONDITIONS

CROSS-REFERENCES TO RELATED APPLICATIONS

The present application is a continuation-in-part application which claims the priority benefit under 35 U.S.C. 119(e) to U.S. Ser. No. 15/902,897, filed on Feb. 22, 2018, and issued as U.S. Pat. No. 10,311,701 on Jun. 4, 2019, which is a continuation application which claims the priority benefit under 35 U.S.C. 119(e) to U.S. Ser. No. 15/684,747, filed on Aug. 23, 2017, and issued as U.S. Pat. No. 9,905,112 on Feb. 27, 2018, which is a continuation-in-part application which claims priority benefit under 35 U.S.C. 119(e) to U.S. Ser. No. 15/357,745, filed on Nov. 21, 2016, and issued as U.S. Pat. No. 9,779,611 on Oct. 3, 2017, which is a continuation-in-part application which claims the priority benefit under 35 U.S.C. 119(e) to U.S. Ser. No. 15/156,503, filed on May 17, 2016, which claims priority to U.S. Provisional Application No. 62/317,844, filed on Apr. 4, 2016, and U.S. Provisional Application No. 62/163,220, filed on May 18, 2015. U.S. application Ser. No. 15/684,747, filed on Aug. 23, 2017, is also a continuation-in-part application which claims priority benefit under 35 U.S.C. 119(e) to U.S. Ser. No. 14/967,027, filed on Dec. 11, 2015, which claims priority to U.S. Provisional Application No. 62/163,220, filed on May 18, 2015, and U.S. Provisional Application No. 62/095,598, filed on Dec. 22, 2014. The present application is also a continuation-in-part application which claims the priority benefit under 37 U.S.C. 119(e) to U.S. Ser. No. 15/479,011 filed on Apr. 4, 2017, and issued as U.S. Pat. No. 10,296,187 on May 21, 2019, which claims priority to U.S. Provisional Application No. 62/317,844, filed on Apr. 4, 2016. The entire disclosures of the above applications are hereby incorporated by reference, for all purposes, as if fully set forth herein.

BACKGROUND

This specification relates in general to generating context-based evaluations of current conditions and, but not by way of limitation, to generating context-based evaluations pertaining to dependent users.

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable outcomes.

BRIEF DESCRIPTION OF THE DRAWINGS

Various embodiments in accordance with the present disclosure will be described with reference to the drawings, in which.

DETAILED DESCRIPTION

The ensuing description provides preferred exemplary examples(s) only, and is not intended to limit the scope, applicability, or configuration of the disclosure. Rather, the ensuing description of the preferred exemplary examples(s) will provide those skilled in the art with an enabling description for implementing a preferred exemplary example. It is understood that various changes may be made in the function and arrangement of elements without departing from the spirit and scope as set forth in the appended claims.

Figure 1:
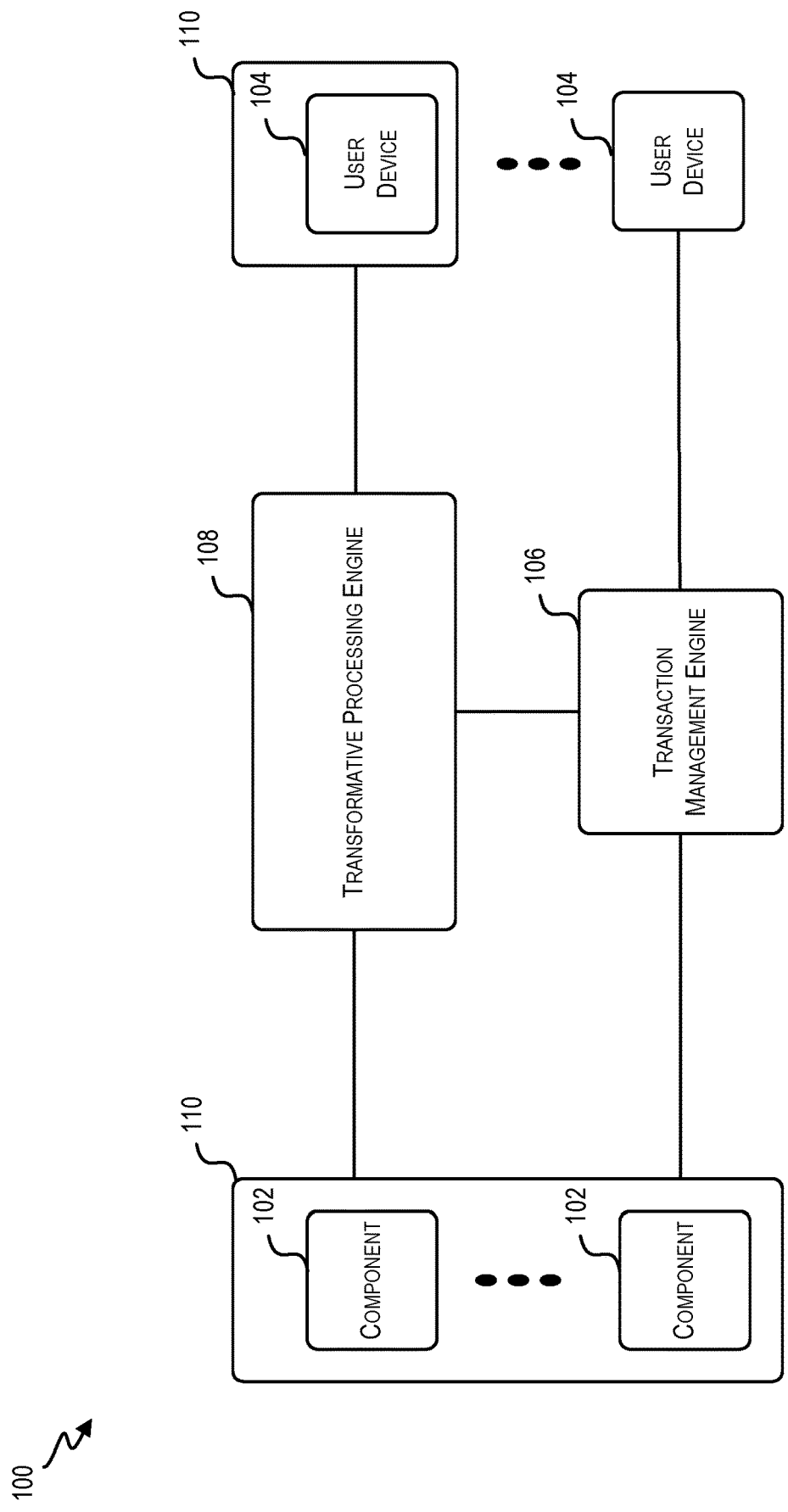
FIG. 1 is an example block diagram illustrating an environment in which techniques relating to generating context-based evaluations of current conditions and generating contextual suggestions for authorized users as described herein may be implemented, according to at least one example.

Referring first to FIG. 1, a block diagram of an embodiment of an interaction system 100 is illustrated. Generally, in interaction system 100, data can be generated at one or more system components 102 and/or user devices 104. Transaction management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect user input received at a user interface of the device. The user input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect user input requesting particular data, to generate a request communication (e.g., to be sent to transformative processing engine), to receive the requested data and/or to present the received data.

Data can include information that identifies a person, such as personal information and/or demographic information. For example, the information can identify a person's name, age, sex, race, physical address, phone number, email address, and/or social security number. Data may include information collected by a government agent, employer, insurer, or school or university, that relates to a past, present, or future condition or status (e.g., pertaining to employment, political involvement, occupation, health, or financial status) of any individual. For example, data may include information about past events.

Data may identify an entity being evaluated and/or one at least partly performing an evaluation. For example, a communication may identify a first company as one being evaluated and a second company as one evaluating a quality of a product of the first company. As another example, a communication may identify a first service plan of a first company as one providing an Internet network and may identify one or more users providing speed checks over the network.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or transaction management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or processing focus. Exemplary types of facilities include server farm facilities, web-server facilities, data-storage facilities, technical-support facilities, telecommunication facilities, care facilities, and/or business operation facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, user accessibility, location, managing client, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and transaction management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., transaction management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. Such storage may enable facility 110 to retain locally data pertaining to its facility prior to (or in conjunction with) the data being shared with transformative processing engine 108 and/or transaction management engine 106. In some examples, the one or more servers of facility 110 share data directly with a record service (not shown), and the record service makes the data available to transformative processing engine 108 and/or transaction management engine 106. Once an electronic record is updated at facility 110, an indication of the update may be provided to the record service. The record service may then update a corresponding record associated with the electronic record.

The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Facility 110 can include one at which a resource is located and/or service is provided. Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
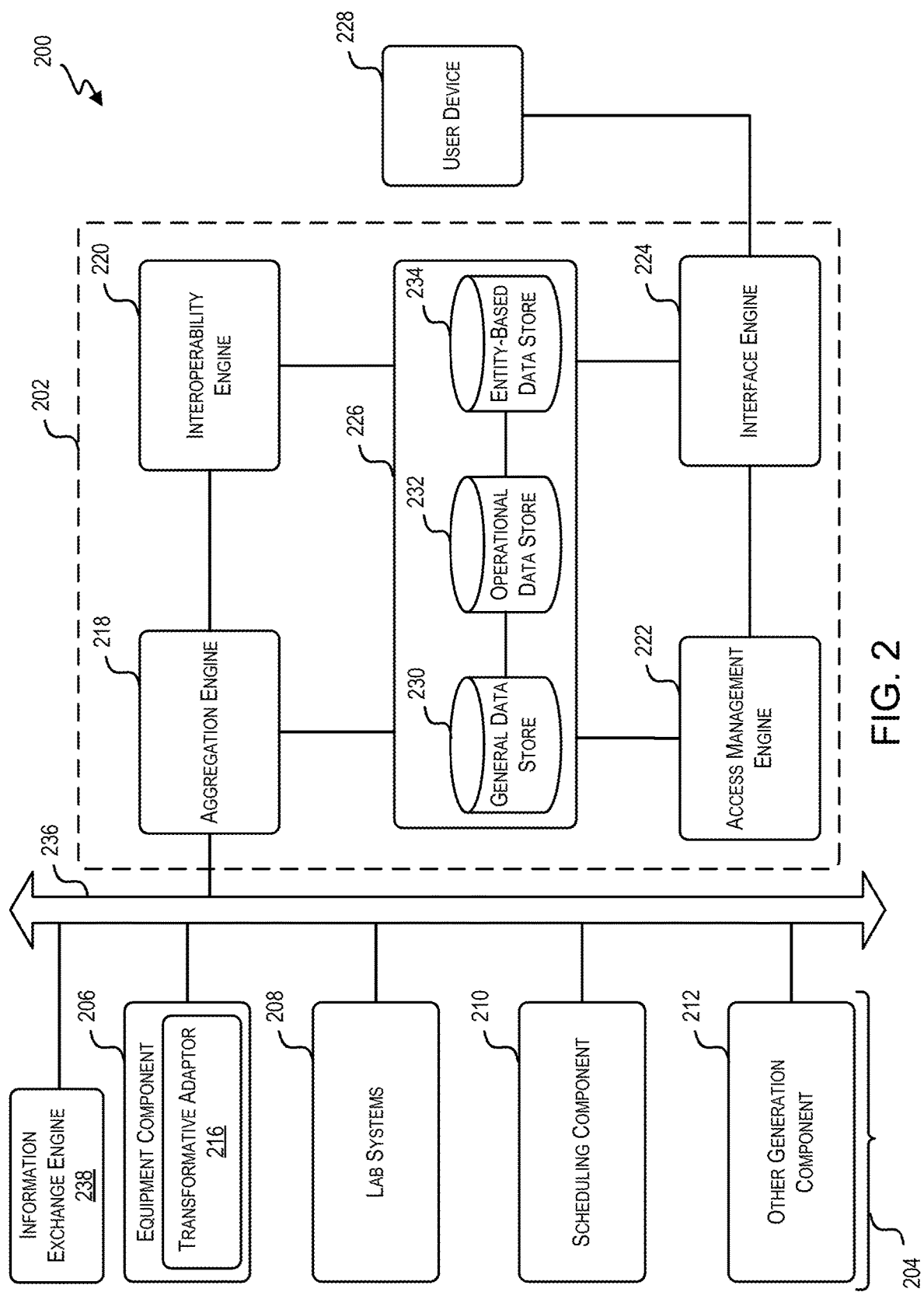
FIG. 2 is an example block diagram illustrating an environment in which techniques relating to generating context-based evaluations of current conditions and generating contextual suggestions for authorized users as described herein may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a scheduling component 210, and other generation component 212. One or more generation components 204 are examples of one or more components 102 discussed with reference to FIG. 1. In some examples, the data may pass to the transformative processing engine 202 via an information exchange service bus 236 (e.g. an enterprise service bus). In some examples, only a portion of the data is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein (e.g., an exposure evaluation engine 922 and a suggestion engine 902). In some examples, the generation components 204 provide data to the transformative processing engine 202 via a messaging bus (e.g., a messaging bus 924 and an information exchange service bus 236). The messaging bus, which may be included in the transformative processing engine 202 or separate, is able to see data that moves throughout the interaction system 200. The messaging bus and information exchange service bus 236 also include a subscription registry that can be used to manage subscriptions to the messaging bus and information exchange service bus 236 for certain data (e.g., data having certain characteristics). The messaging bus and information exchange service 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Scheduling component 210 includes any suitable computing devices used for business-related purposes with respect to interaction system 200. For example, scheduling component 210 can be configured to schedule a resource for allocation for a particular entity during a particular time slot. Scheduling component 210 can monitor a schedule for the resource and can identify one or more available time slots that may be secured by a particular entity. Upon receiving a scheduling indication, scheduling component 210 may update a schedule of a resource to reflect that a particular time slot is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the data provided by the component or the user device located at the geographic location.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, have paid a subscription fee associated with access to data store 226, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized users (e.g., dependent users, friends and family members of dependent users, professional users, and other suitable authorized users). The information exchange engine 238 is also configured to route inbound messages and route outbound messages, as described herein. The information exchange engine 238 is also configured to generate customized messages based on dependent user data and professional users.

Figure 3:
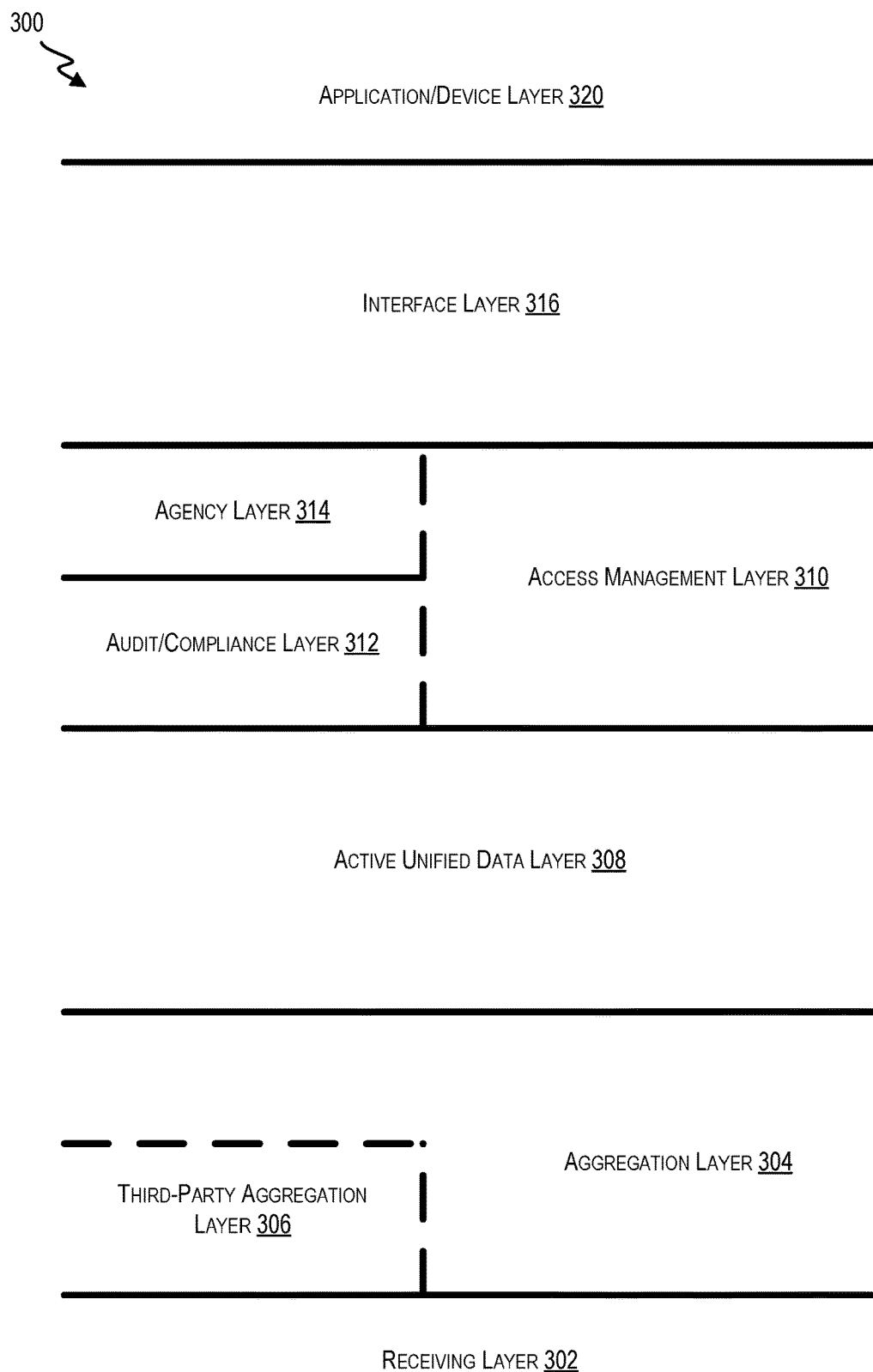
FIG. 3 is an example schematic model illustrating a network communication model in which techniques relating to generating context-based evaluations of current conditions and generating contextual suggestions for authorized users as described herein may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
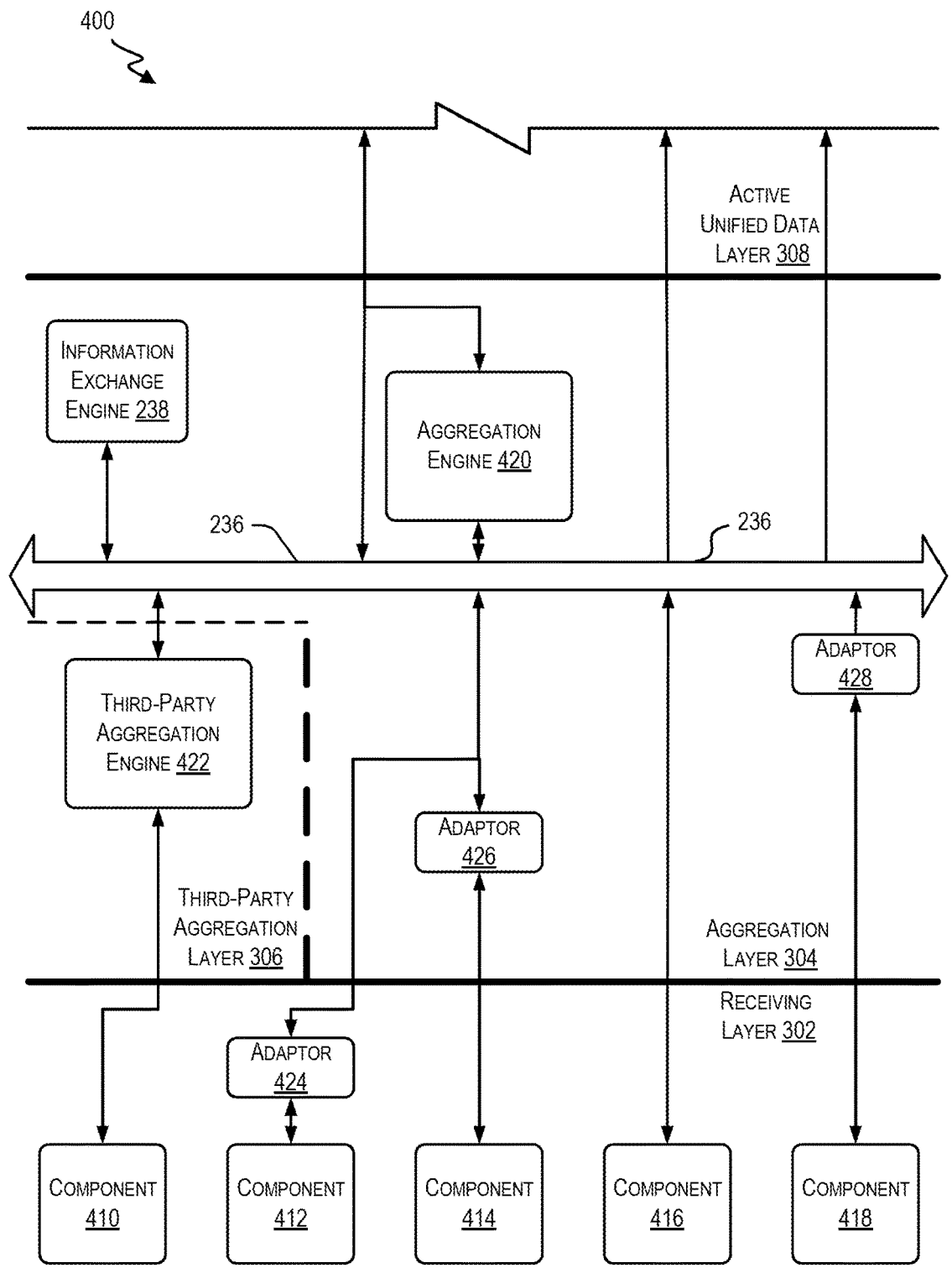
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
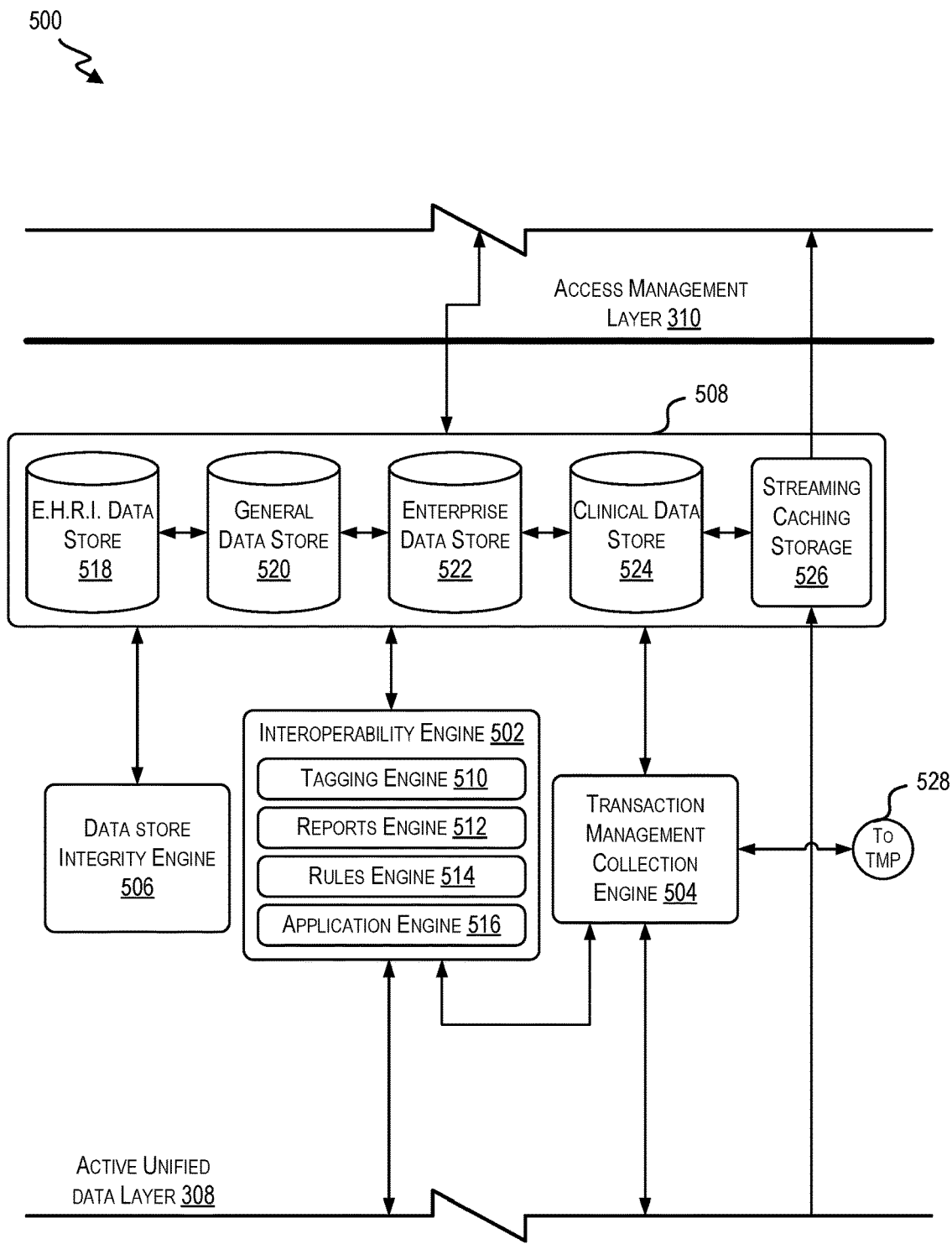
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a transaction management collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Transaction management collection engine 504 is implemented as part of transaction management engine 106. Transaction management collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), transaction management engine 106 (e.g., transaction management collection engine 504 of transaction management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to transaction management engine 106 that it saw the message. In this manner, transaction management engine 106 may enable end-to-end tracking of messages for the life of the message.

In one example, the messages are requests. The requests may be generated based on user input at one of the components. The requests may be received by transformative processing engine 108 and integrated into the system. In some examples, transaction management engine 106 may be notified that the requests have been received and may therefore be configured to generate message IDs for each request. These message IDs may then be associated with each of the requests. As the requests continue to move throughout the interaction system (e.g., away from transformative processing engine 108), transaction management engine 106 may be track their movement using the message IDs. If one of the requests does not make it to its destination, transaction management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, transaction management engine 106 (e.g., transaction management collection engine 504 of transaction management engine 106) may receive the message and/or message identifier directly from one of components 410-418. For example, one of components 410-416 may be configured to generate the unique message identifier and/or communicate directly with transaction management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, transaction management collection engine 504 provides unique message identifiers to other elements of the interaction system to monitor the messages as they move throughout the interaction system. Transaction management collection engine 504 also provides a portion of the unique message identifiers to a transaction management platform (indicated by a circle 528) for further analysis of the message identifiers. Such analysis may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage business rules, condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("record data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within record data store 518 is retained data including electronic record information. In some examples, the information within record data store 518 is organized according to entity identifying information. Thus, record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used by conventional business concerns.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of personal record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
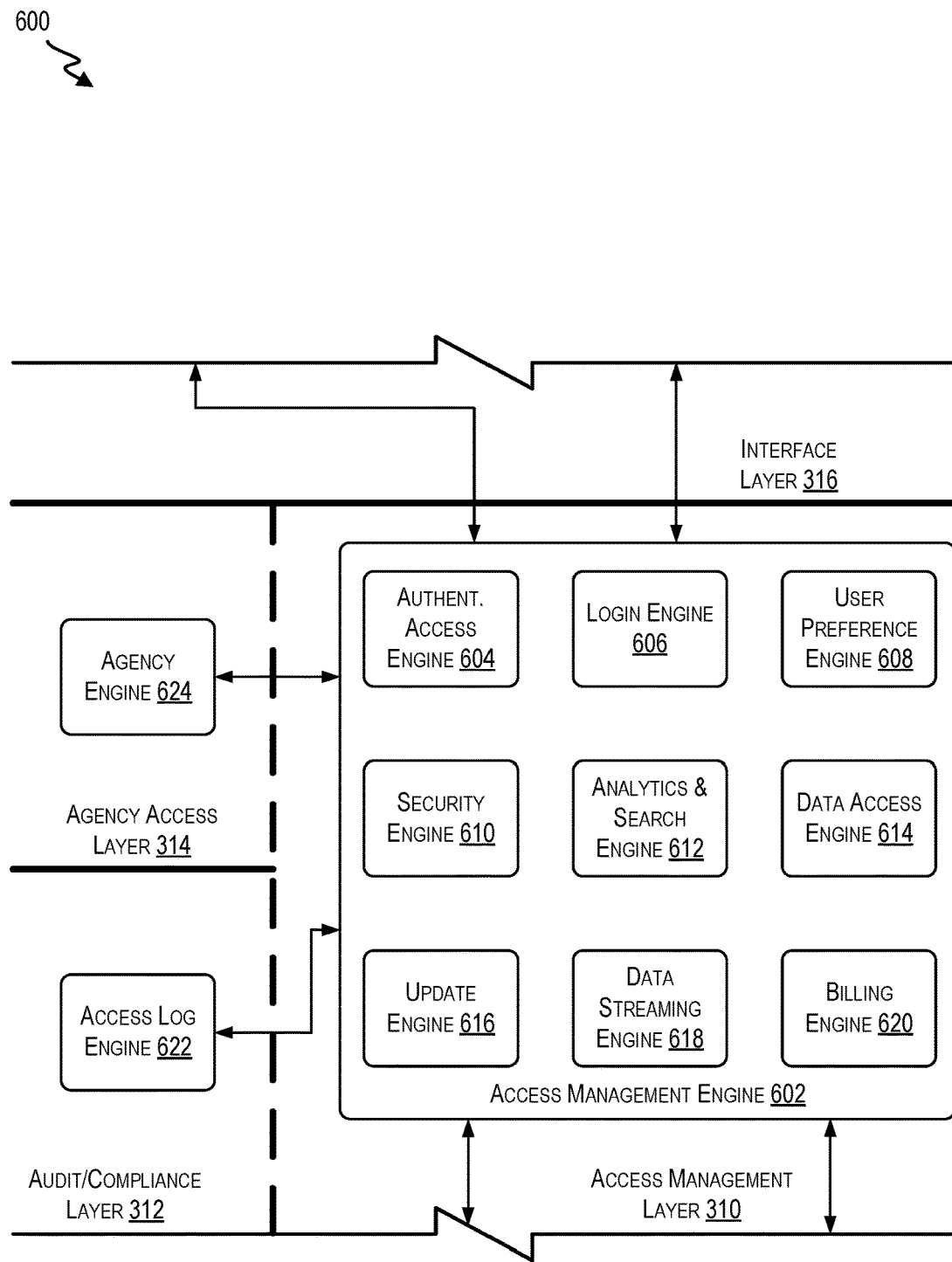
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. For example, agencies that may use agency engine 624 include agencies to which the interaction system provides compliance, tracking, or other reporting information. For example, agency engine 624 may be used to track one or more performance indicators identified by a government agency and/or to provide report instances of defined types of events. Thus, in some examples, a government agency uses agency engine 624 to collect data pertaining to compliance of the interaction system with one or more statutes or regulations. In some examples, a university is an agency that uses agency engine 624 to collect data pertaining to one or more studies. In some examples, agency engine 624 can identify one or more entities (e.g., governmental agencies) that are to receive reports pertaining to operations or events and what types of data are to be reported to those entities. Agency engine 624 can then collect the pertinent data, potentially format and/or analyze the data, and facilitate transmission of (e.g., raw, formatted and/or analysis of) the data to the appropriate agency.

Figure 7:
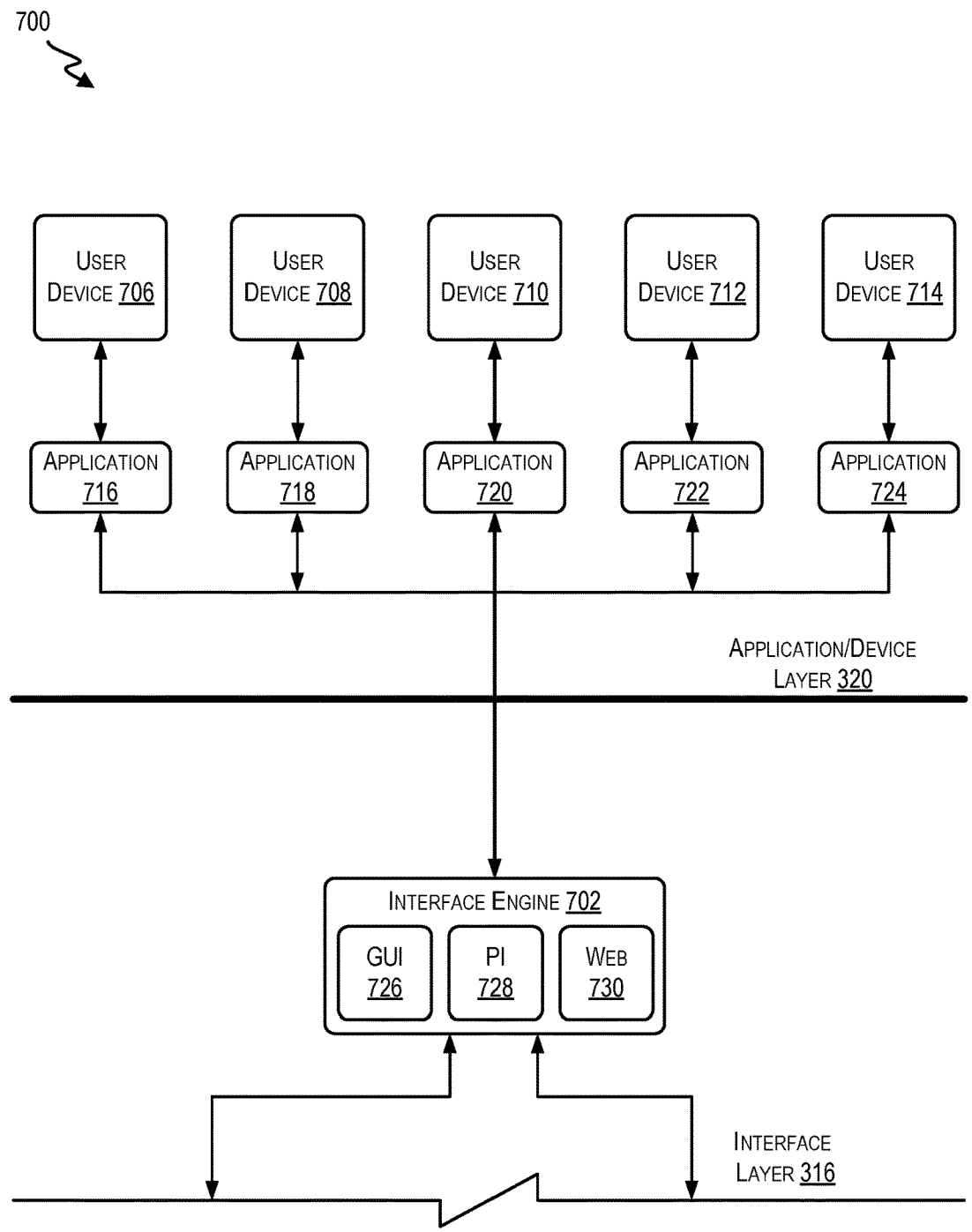
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a specialty associated with the entity and protected information associated with the entity. In this manner, application 720 adapts and automatically adjusts depending on the context in which the entity is using the application. In some examples, the data indicates performance statistics for the entity, metrics relating to where the entity falls along a distribution of other similar entities, outlier instances, trends in events or actions, and the like. Application 720 may be configured to receive input, adjust presentations, present unprompted alerts, adjust display of content, move more relevant content to the foreground, move less relevant content to the background, populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

In some examples, application 724 may be a business intelligence application. In this example, application 724 is used to display business information generated by components of the interaction system. This business information can be used for operations, planning, and forecasting. Such business information may include data because such data may impact operations, planning, forecasting, and the like. Accordingly, application 724 may present de-identified information in the form of one or more metrics, indicators, or the like as they pertain to business intelligence.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
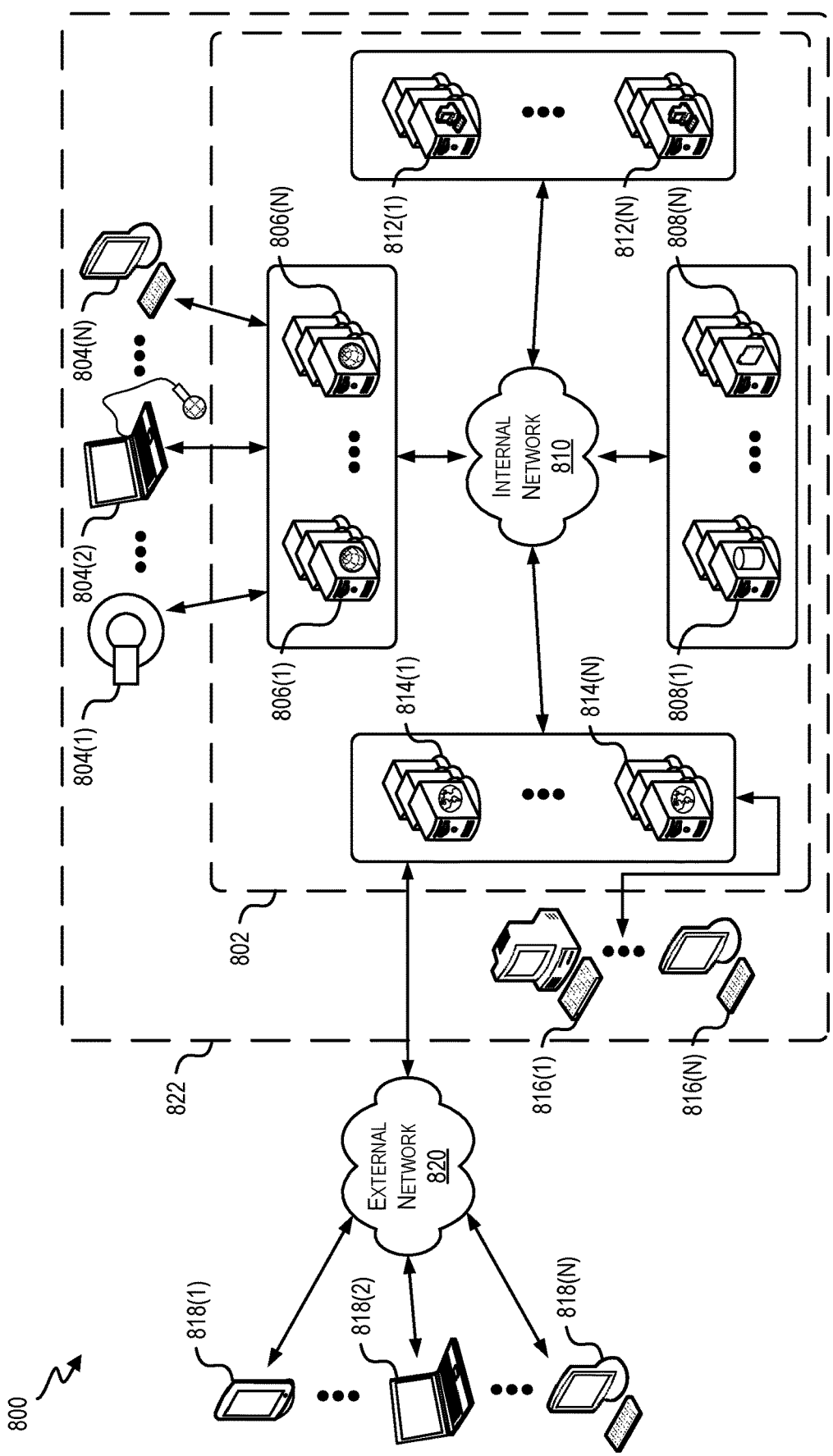
FIG. 8 is an example schematic architecture illustrating a network in which techniques relating to generating context-based evaluations of current conditions and generating contextual suggestions for authorized users as described herein may be implemented, according to at least one example.

Turning now to FIG. 8, an interaction system 800 is shown in accordance with at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

The environments, systems, networks, models, and the like of FIGS. 1-8 may be used to implement the techniques described herein and techniques described in U.S. Ser. No. 14/967,027, filed on Dec. 11, 2015; U.S. Ser. No. 15/479,011, filed on Apr. 4, 2017; U.S. Provisional Application No. 62/095,598, filed on Dec. 22, 2014; and U.S. Provisional Application No. 62/317,844, filed on Apr. 4, 2016; the disclosures of each of which applications are incorporated by reference herein in their entireties for all purposes, as if fully set forth herein. For example, in one example described herein, a suggestion engine is provided that generates suggestions within a provider network. The suggestion engine accesses information from many different sources in order to make informed suggestions that are particularized to a dependent user and/or an authorized user. For example, as an authorized user initiates an order corresponding to present conditions of the dependent user, the suggestion engine begins to determine a list of suggestions. To do so, the suggestion engine considers a profile of the authorized user and the dependent user's record (e.g., dependent user's present conditions, demographic information, history, etc.). This information helps to provide context to what suggestions would be helpful for the authorized user to address the current conditions of the dependent user within a particular scenario. In addition, the suggestion engine considers a knowledge base organized into what are referred to herein as knowledge artifacts. The knowledge artifacts represent associations between certain situations (e.g., orders, diagnoses, etc.) and the outcomes in related cases. Some knowledge artifacts are determined programmatically or by human users from proprietary information within the provider network. Other knowledge artifacts are determined from information collected from sources external to the provider network. The suggestion engine considers the knowledge artifacts by comparing them to the scenario to determine a list of suggestions. The suggestion engine also considers costs associated with the list of suggestions, availability of the suggestions, payment constraints, and any other relevant factor that would be considered by an authorized user in determining a recommended course of treatment. These suggestions are then weighted by the outcomes associated with each suggestion. In this manner, the list of suggestions represents a list of likely orders, steps, acts, tests, procedures, or the like that the authorized user should consider while administering attention to the dependent user.

In another example, an exposure evaluation engine is provided. The exposure evaluation engine is configured to monitor, collect, and/or receive structured and unstructured data from a data warehouse and/or streamed from data storage and processing systems (e.g., record services), or components (e.g., devices that generate data) of a provider network in real-time. The structured and unstructured data corresponds to records of users, actions taken on behalf of users, and the like. The exposure evaluation engine analyzes the structured data and the unstructured data in order to determine whether a user is at risk for developing an abnormal condition, and whether to include the results of the analysis in an exposure evaluation. The exposure evaluation indicates the abnormal condition, identifies the user, and includes certain information to enable an authorized user to make a decision of how to respond to the exposure evaluation (e.g., decision support output). For example, the exposure evaluation may indicate a likelihood that the user will develop an abnormal condition in order to allow the appropriate user to take guided action. The exposure evaluation engine is configured to parse through the structured and unstructured data in a manner that enables the exposure evaluation engine to develop conclusions and/or make assessments about the condition quicker and across broader data sets than a typical authorized user and on a real-time basis as new data arrives that impacts a user's exposure evaluation. In some examples, because the exposure evaluation engine parses unstructured data (not just structured data), which may include subjective information, the exposure evaluation engine may be able to draw conclusions and "see the big picture" of the condition of the user. Once the exposure evaluation for the user has been generated, it is included in a notification that can be sent to any number of suitable recipients. For example, the notification can be sent to a coordinator of a physical location or an authorized user who can take the next steps based on the exposure evaluation.

Figure 9:
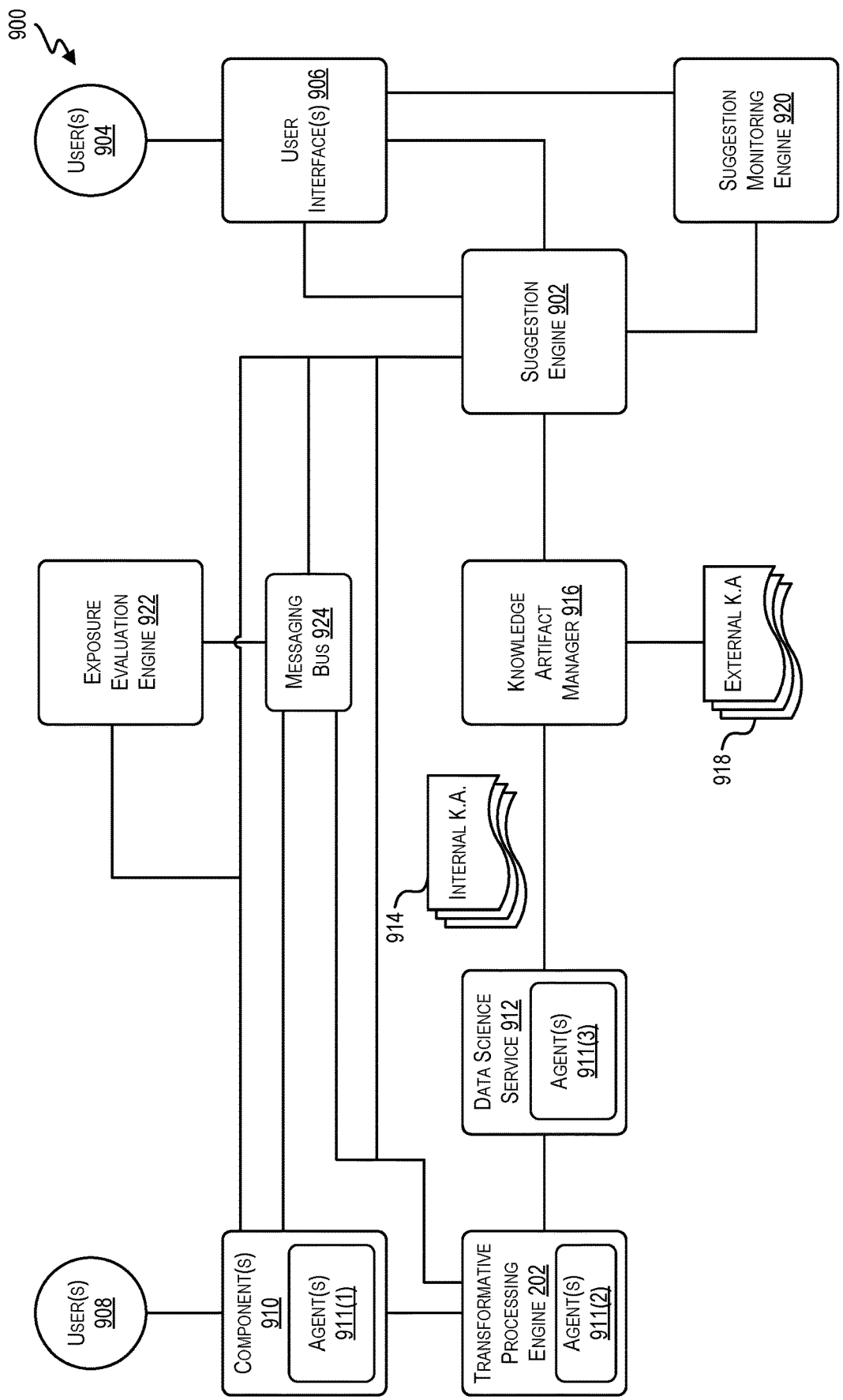
FIG. 9 is an example block diagram illustrating an environment in which techniques relating to generating context-based evaluations of current conditions and generating contextual suggestions for authorized users may be implemented, according to at least one example.

FIG. 9 illustrates an environment 900 in accordance with at least one example. The environment 900 may be implemented using at least some of the elements of the interaction system 800. The environment 900 includes a suggestion engine 902, which is configured to implement at least some of the techniques described herein. For example, the suggestion engine 902 generates suggestions (e.g., contextual jobs including suggested jobs, suggested tasks, and the like) that can be provided to receiving users 904 via one of more user interfaces 906. In order to generate the suggestions, the suggestion engine 902 accesses data from a variety of different sources, a few of which are illustrated in FIG. 9. In some examples, the creation of such data begins with generation users 908. The generation users 908 and the receiving users 904 may come from the same group of users and may be similar to the users that operate the components 410-418 and/or the users that operate the user devices 706-714. Accordingly, the generation users 908 interact with components 910 to generate at least some of the data used for generating the suggestions. The components 910 are examples of the components 410-418 discussed herein. In some examples, the data includes data that indicates actions performed by the users 908. For example, when user 908 accesses and/or edits a record belonging to the user or a different user, interacts with an ordering application, opens and practices management application, and/or performs any other comparable action, data can be generated.

The data generated by the users 908 interacting with the components 910 is provided to the transformative processing engine 202. In response, the transformative processing engine 202 performs one or more operations on the data such as those discussed herein. One of the operations includes the transformative processing engine 202 retaining the data in a manner that makes it searchable and useable by other elements of the environment 900. For example, a data science service 912 interacts with the transformative processing engine 202 to access the data stored thereby. The data science service 912 analyzes the data retained by the transformative processing engine 202 to give the data meaning. For example, the data science service 912 evaluates the data to identify trends in the data or correlations between different data that could be valuable for treatment of dependent users associated with authorized users. Identified trends, correlations, and other outputs (e.g., evidence of patterns, outcomes, and the like) identified from the data by the data science service 912 are referred to herein as internal knowledge artifacts 914. The internal knowledge artifacts 914 are provided to a knowledge artifact manager 916.

The data science service 912 includes human users accessing computing devices to generate the internal knowledge artifacts 914. Generating the internal knowledge artifacts 914 may include adjusting relevant data into one or more formats, particular data structures, or the like that can be read by the suggestion engine 902 when generating suggestions. A computing device of the data science service 912 may be any conventional computing device including a memory, processor, operating system, and the like for generating the internal knowledge artifacts 914. The data science service 912 may also include one or more automated engines within a computing device, or distributed throughout many computing devices. The engines may be configured to analyze the data and generate internal knowledge artifacts 914 programmatically. For example, the data science service 912 may include a learning engine that analyzes the data to identify trends, correlations, patterns, and the like in a similar manner as the human users described above. The internal knowledge artifacts 914, whether generated with the assistance of human users or generated programmatically, are provided to the knowledge artifact manager 916 that manages the internal knowledge artifacts 914. This may include organizing the internal knowledge artifacts 914 in a manner useable by the suggestion engine 902. To this end, the knowledge artifact manager 916 may include a memory, which may be distributed among many different devices.

The knowledge artifact manager 916 also receives external knowledge artifacts 918. The external knowledge artifacts 918 are generated by organizations, users, and others that fall outside of the organization that operates the environment 900. The external knowledge artifacts 918 and the internal knowledge artifacts 914 represent associations between certain treatment patterns and outcomes in the related cases. In some examples, the knowledge artifact manager 916 is not included in the environment 900 and the internal knowledge artifacts 914 and the external knowledge artifacts 918 are made available directly to the suggestion engine 902.

When the knowledge artifact manager 916 is included in the environment 900, the knowledge artifact manager 916 manages all of the knowledge artifacts. To this end, the knowledge artifact manager 916 performs operations on the knowledge artifacts 914, 918 to retain them in the memory of the knowledge artifact manager 916 in a manner and format that is accessible by the suggestion engine 902. In some examples, once the knowledge artifact manager 916 receives the internal knowledge artifacts 914 and the external knowledge artifacts 918, the knowledge artifact manager 916 compares the different knowledge artifacts and may identify knowledge artifacts based on a combination of the internal knowledge artifacts 914 and the external knowledge artifacts 918. The knowledge artifact manager 916 receives the internal knowledge artifacts 914 and the external knowledge artifacts 918 on an ongoing basis. In some examples, the knowledge artifacts 914, 918 are sent to the knowledge artifact manager 916 periodically, when requested by the knowledge artifact manager 916, in accordance with a user-defined rule or a machine-defined rule (e.g., send in batches consisting of a pre-defined number or size of knowledge artifacts), or in any other suitable manner. The knowledge artifact manager 916 in turn provides the knowledge artifacts 914, 918 to the suggestion engine 902 periodically, when requested by the suggestion engine 902, in accordance with a rule, or in any other suitable manner. In some examples, the suggestion engine 902 does not receive the knowledge artifacts 914, 918, but accesses them when needed. Thus, the internal knowledge artifacts 914 and the external knowledge artifacts 918 can be considered data.

The data can be identified by one or more agents 911 that are included in the components 910, the transformative processing engine 202, and the data science service 912. The agents 911 can include any suitable combination of software and/or hardware elements configured to execute within these devices and/or otherwise access data generated by these devices. In some examples, the agents 911 are installed in all components 910 (and other devices), but are only activated when particular applications and/or processes are running on the components 910 (and other devices). The agents 911 function to monitor data generated or otherwise processed by the components 910 (and other devices) to detect data having certain characteristics. For example, data that identifies a dependent user (e.g., via a user identifier) or is otherwise associated with the dependent user, may be detected by the agents 911. Once detected, the agents 911 coordinate sending of the data to the other elements of the environment 900 (e.g., the suggestion engine 902 and an exposure evaluation engine 922).

The suggestion engine 902 accesses the knowledge artifacts 914, 918 and based on other data, generates suggestions. The suggestion engine 902 accesses the data in real-time or substantially real-time. Data includes real world conditions data, specific details about a dependent user (e.g., data associated with a record of the dependent user), and details about attention scenarios of the dependent user for which the suggestion engine 902 will make the suggestions. For example, the suggestion engine 902 may receive data in the form of output from a computerized treatment machine (e.g., one of the components 910). The output may be associated with a dependent user who was receiving treatment by the computerized treatment machine. The suggestion engine 902 accesses the output, which identifies the particular dependent user, and runs through a list of potentially-relevant knowledge artifacts that may assist the suggestion engine 902 in making a suggestion to an authorized user who is authorized to attend to the particular dependent user. For example, the suggestion engine 902 may determine that, based on a knowledge artifact (external, internal, or a combination) dealing with kidney failure, a particular drug may be helpful for the particular dependent user. This information (i.e., recommended drug) is then provided to the authorized user, who is one of the receiving users 904, as a suggestion, with an option to automatically place an order for the drug. In this manner, the contextual suggestions described may be based on the current data, knowledge artifacts, and output parameters and configuration settings (e.g., user-defined and machine-defined (e.g., learned) rules that define what output will be presented, how it will be presented, and other details about presentation) of certain components 910.

The suggestion engine 902 may interact using the active unified data layer 308 or the access management layer 310. In some examples, at least a portion of the interactions of the suggestion engine 902 take place in the interface layer 316 and/or the application/device layer 320. In this manner, the suggestion engine 902 may be configured to provide suggestions to the user interfaces 906 via the interface layer 316 and/or the application/device layer 320. The user interfaces 906 are examples of the user interfaces capable of generation by the interface engine 702 and may be accessed by the receiving users 904 using applications running on user devices as described herein. The suggestion engine 902 provides the suggestions to the user interfaces 906 by sending the suggestions in accordance with an earlier subscription and/or by publishing the suggestion to a common location, which may be accessed by an application supporting the user interface 906 (e.g., via one or more application programming interfaces (API) calls).

The environment 900 also includes a suggestion monitoring engine 920. The suggestion monitoring engine 920 is configured to monitor the suggestion engine 902. This may include, for example, comparing suggestions generated by the suggestion engine 902 with result data characterizing whether authorized users acted on the suggestions, ignored the suggestions, or in some other way acknowledged the suggestions. Such result data is collected from the receiving users 904 via the user interfaces 906 or directly from users devices on which the receiving users 904 interact in some other way. In some examples, the result data is collected over time and provided to the suggestion monitoring engine 920 periodically. In this manner, the suggestion monitoring engine 920 may ensure that the suggestions generated by the suggestion engine 902 are current, correct, and meaningful. The suggestion monitoring engine 920 is configured to adjust the weight of previously made suggestions if those suggestions are not being acknowledged. The suggestion monitoring engine 920 also outputs reports, alerts, signals, and the like pertaining to suggestions. Such reporting may include recommendations to operators of the environment 900 regarding adjustments to the suggestion engine 902, the knowledge artifact manager 916, the user interfaces 906, or any other element of the environment 900.

The environment 900 also includes an exposure evaluation engine 922. As described in further detail herein, the exposure evaluation engine 922, like the suggestion engine 902, receives data from a variety of different elements of the environment 900. In some examples, this exposure-relevant data is similar to the data described herein with reference to the suggestion engine 902. The exposure-relevant data may include structured data and unstructured data. The exposure-relevant data may be associated with a dependent user, a group of dependent users, an authorized user, a group of authorized users, a physical location, a geographical region, and the like. The exposure evaluation engine 922 may include functionality to analyze the structured data and the unstructured data as part of generating exposure evaluations for dependent users. An example exposure evaluation may indicate whether a dependent user has a particular condition or is likely to get the particular condition. The exposure evaluation may be shared with the receiving users 904 via the one of more user interfaces 906 as a notification. The content of the notification may depend on the likelihood present in the exposure evaluation. The receiving users 904 may be selected such that the notification is provided to those users who are responsible for tending to the dependent user and/or addressing the particular condition included in the exposure evaluation. The user interfaces 906 and/or applications used to present the notifications may be selected to emphasize certain notifications over others (e.g., cause notifications including more critical exposure evaluations to be viewed prior to those with less critical evaluations). In some examples, unstructured data (e.g., letters, numbers, and symbols stored in an unknown format) includes subjective observations and the structured data (e.g., letters, numbers, and symbols stored in a known format) includes objective measures.

The transformative processing engine 202 may provide or make available certain types of and/or classes of data to the exposure evaluation engine 922. As described herein, the exposure evaluation engine 922 generates a particular class of decision support output. For example, the exposure evaluation engine 922 generates exposure evaluations (e.g., predictions and deterioration assessments) based on data accessed from the transformative processing engine 202, the components 910, the suggestion engine 902, the knowledge artifact manager 916, and/or other comparable elements or entities. To this end, the exposure evaluation engine 922 includes one or more rule sets that can be evaluated to determine whether certain input information (e.g., input data) triggers one or more outputs. For example, the exposure evaluation engine 922 may use real-time data received from the transformative processing engine 202 and/or from one of the components 910 to determine whether a dependent user has early symptoms of sepsis, heart disease, cancer, etc. In some examples, the exposure evaluation engine 922 identifies such symptoms earlier than a reasonable authorized user would be able to. This may be because the exposure evaluation engine 922 is configured to evaluate, in real-time, objective and subjective data from many different sources in order to determine the exposure evaluation. Even when the data is not real-time data, the exposure evaluation engine 922 nevertheless may generate an exposure evaluation earlier than a typical authorized user because the exposure evaluation engine 922 is configured to evaluate very large data sets of data, and to draw conclusions and/or inferences from the data that would be time prohibitive for the typical authorized user. This may be important in cases where the exposure evaluation includes a condition that includes a very tight window for treatment. In some examples, once the exposure evaluation engine 922 draws a conclusion from the data, this conclusion can be included in a notification, which can be provided to the users 904. In some examples, the exposure evaluation includes an authorized indication of a particular condition. In some examples, the exposure evaluation functions to notify an authorized user that a dependent user with an existing condition is deteriorating. The exposure evaluation can also be provided to the transformative processing engine 202 where it can be verified by an authorized user or otherwise to determine whether the exposure evaluation, including the authorized indication and deterioration assessment, are correct.

In some examples, at least a portion of the data used by the exposure evaluation engine 922 is received from the data science service 912 in the form of one or more knowledge artifacts. The one or more knowledge artifacts are characterized as objective data or subjective data depending on the type and class of the artifacts.

Once an exposure evaluation or other type of decision support output has been generated by the exposure evaluation engine 922, the exposure evaluation is provided directly to the user interface 906 to be consumed by one of the receiving users 904. This includes, for example, providing the exposure evaluation (or a notification including at least a portion of the exposure evaluation) into an existing workflow. In some examples, the exposure evaluation is provided to a computing device of a facility that is accessible to one or more authorized users during a predetermined period of time. The exposure evaluation, in this example, indicates the dependent user, a condition associated with the dependent user (whether current or possible), a likelihood that the dependent user will develop the condition, and any other suitable information.

In some examples, the exposure evaluation or other decision support output is provided to the suggestion engine 902, and the suggestion engine 902 generates a suggestion based on the exposure evaluation. The suggestion engine 902 then provides the suggestion, which may include the exposure evaluation, to the receiving users 904 via the user interfaces 906 as described herein. Thus, the suggestion engine 902 can use the exposure evaluation as input to generate contextual jobs for the authorized user, as described herein.

The exposure evaluation engine 922 may interact using the active unified data layer 308 or the access management layer 310. In this manner, the exposure evaluation engine 922 is configured to gather data (e.g., input signals) from those elements that generate data and/or store data. In some examples, at least a portion of the interactions of the exposure evaluation engine 922 take place in the interface layer 316 and/or the application/device layer 320. In this manner, the exposure evaluation engine 922 may be configured to provide notifications and other messages relating to exposure evaluations to the user interfaces 906 via the interface layer 316 and/or the application/device layer 320. Thus, the notifications may be provided to the user devices (e.g., the user devices 706-714) via the application/device layer 320. Similarly, the notifications may be provided to the user interfaces 906 via the interface layer 316.

The environment 900 also includes a messaging bus 924 (e.g., an enterprise service bus). The messaging bus 924 is configured to monitor messages that flow across the messaging bus 924. In some examples, a user may send a subscription request to the messaging bus 924. The subscription request may request that certain data (e.g., messages, signals, etc.) having certain data attributes be directed to any one of the elements of the environment 900. For example, data may be detected by the messaging bus 924 and directed to the exposure evaluation engine 922 and/or the suggestion engine 902 to perform the techniques described herein. In some examples, the subscription requests to the messaging bus 924 are generated in response to user input at one of the components 910 (e.g., a user device). In other examples, the subscription requests to the messaging bus 924 are generated in response to detection of an event or certain data. For example, when a record is created for a new dependent user and saved by the transformative processing engine 202, a subscription request may be generated that identifies the dependent user (e.g., by a unique user identifier) and requests notification when the record is updated. Such notifications from the messaging bus 924 may be used by the suggestion engine 902 to generate suggestions for responding changes in the record (e.g., a change to current conditions that may require attention from an authorized user). Such notifications from the messaging bus 924 may also be used by the suggestion engine 902 to detect an actionable event (e.g., an event that prompts the suggestion engine 902 to generate contextual jobs). Such notifications from the messaging bus 924 may also include monitoring requests received from an authorized user and identifying a dependent user.

Figure 10:
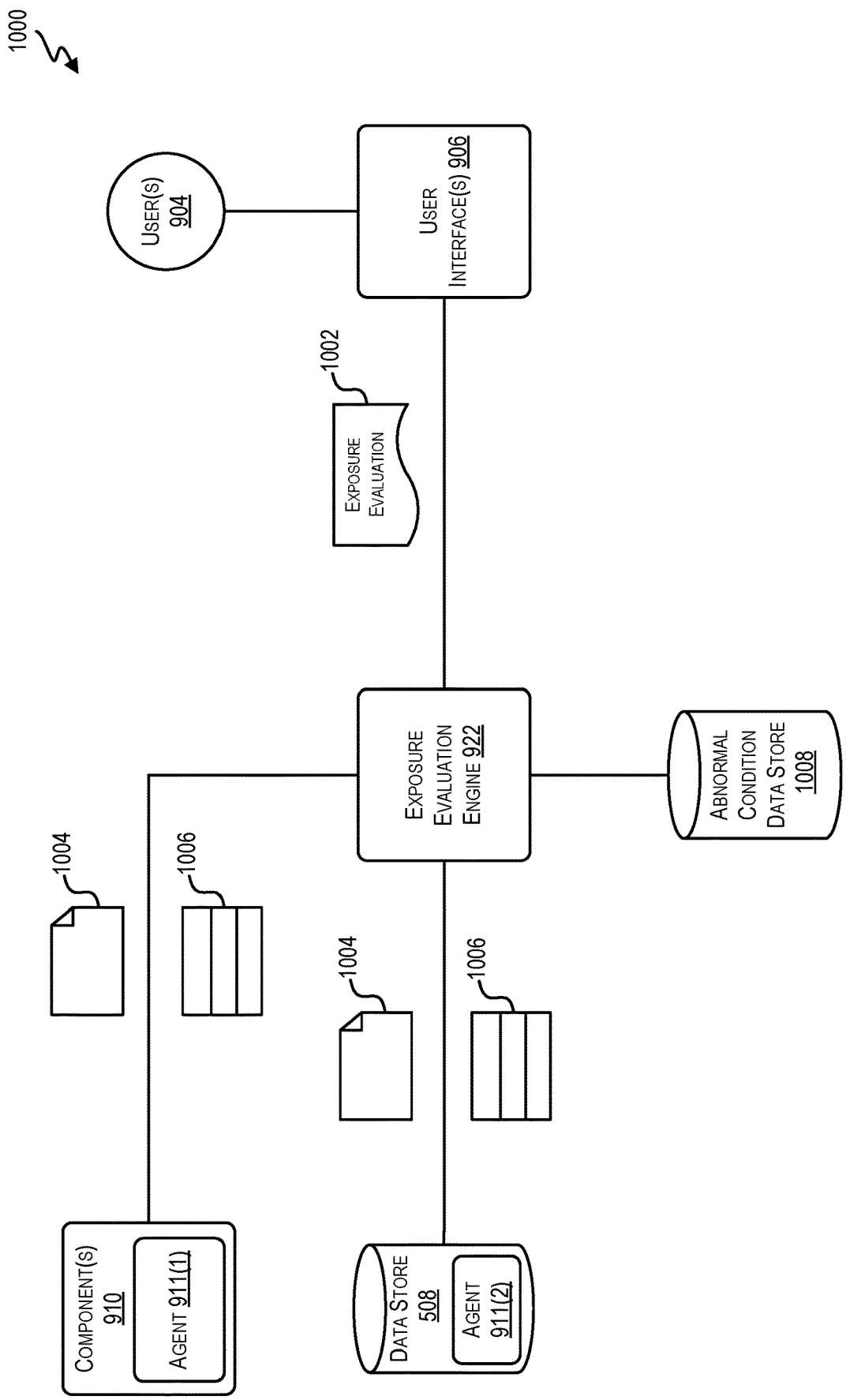
FIG. 10 is an example block diagram illustrating an environment in which techniques relating to generating context-based evaluations of current conditions as described herein may be implemented, according to at least one example.

FIG. 10 illustrates an environment 1000 in accordance with at least one example. The environment 1000 includes the exposure evaluation engine 922 in communication with the data store 508 (associated with the transformative processing engine 202), the user interfaces 906, and an abnormal condition data store 1008. As discussed herein, within the data store 508 is stored data, which is searchable and accessible by the exposure evaluation engine 922. The exposure evaluation engine 922 is configured to access data from the data store 508 and/or from the components 910 in order to generate one or more exposure evaluations 1002. In particular, the exposure evaluation engine 922 accesses unstructured data 1004 and/or structured data 1006 from the data store 508 and/or the components 910. Thus, in some examples, portions of the unstructured data 1004 and/or portions of the structured data 1006 are received in real-time (e.g., streamed) from the components 910 that generated and/or aggregated the unstructured data 1004 and/or the structured data 1006. In some examples, this may enable the exposure evaluation engine 922 to receive data in real-time (e.g., at the network speed it takes for data to transfer from a component to the exposure evaluation engine 922).

In some examples, the unstructured data 1004 is considered unstructured because the exposure evaluation engine 922 cannot recognize the organization of the data (e.g., a type of subjective data). Thus, in order to derive meaningful information from the unstructured data 1004, the exposure evaluation engine 922 uses one or more natural language processing techniques to analyze the unstructured data 1004. Using these techniques, the exposure evaluation engine 922 identifies not only what words, symbols, and letters are included in the unstructured data 1004, but also parses the unstructured data 1004 to identify meaning, tone, sentiment, humor, sarcasm, and other forms of speech present in the unstructured data 1004. Examples of the unstructured data 1004 include: prose text written by an authorized user and included as an entry in a record of a dependent user or included in some other data structure, graphical depictions prepared by an authorized user and included as an entry in a record of the dependent user or included in some other data structure, prose text or graphical depictions prepared by a dependent user, a person related to the dependent user, and any other suitable unstructured data that can be analyzed by the exposure evaluation engine 922.

In some examples, the structured data 1006 is considered structured because the exposure evaluation engine 922 recognizes the organization of the data (e.g., a type of objective data). This may be because the structured data 1006 is organized in a format that the exposure evaluation engine 922 can interpret. For example, a message that includes the structured data 1006 may have a fixed number of data fields (e.g., three) separated by commas, and may also include a text string in a header of the message that identifies what type of structured data 1006 is included in the message. Deriving meaningful information from the structured data 1006, in some examples, is performed relatively quickly compared to the unstructured data 1004. This is because when parsing the structured data 1006, the exposure evaluation engine 922 expects the format of the structured data 1006, which enables the exposure evaluation engine 922 to determine what data is important and what can be disregarded. Thus, the structured data 1006 may include electronic data that includes discrete data elements organized in a standardized manner. Examples of the structured data 1006 include: results of tests, narrative text that is encoded with discrete data elements, results of customary vital-sign tests, and any other suitable structured data that can be analyzed by the exposure evaluation engine 922.

As part of generating the exposure evaluation 1002, the exposure evaluation engine 922 accesses the abnormal condition data store 1008. In some examples, the abnormal condition data store 1008 includes one or more abnormal conditions for which the exposure evaluation 1002 can be generated and that are associated with one or more conditions of the abnormal condition (e.g., symptoms). The one or more conditions are associated with their respective abnormal conditions and retained in the abnormal condition data store 1008. Thus, for each abnormal condition, there are one or more conditions which are typically present and associated with the abnormal condition. In some examples, the presence of a particular condition is a necessary condition of the abnormal condition. In some examples, the presence of a particular condition is a sufficient condition of the abnormal condition. In some examples, however, the presence of certain sets of conditions in the absence of others, may be a necessary condition of the abnormal condition, a sufficient condition of the abnormal condition, or have no bearing on the determination of the abnormal condition. In some examples, a dependent user may already be diagnosed with one of the one or more abnormal conditions in the abnormal condition data store 1008. In this example, the exposure evaluation engine 922 may evaluate the conditions of the known abnormal condition in order to determine whether the dependent user's condition, with respect to the known abnormal condition, is deteriorating.

An evaluation rule is associated with each of the conditions of the abnormal condition in order to determine whether the input data indicates that the dependent user has the condition. Thus, the evaluation rule indicates what data should be present to identify that the dependent user has the condition. Each evaluation rule may also include a weighting relative to the abnormal condition and a numerical score for each abnormal condition. For example, if condition X is present, the dependent user may be 100% likely to have the abnormal condition or 50% likely to have the abnormal condition. The weighting also takes into account the known details about the dependent user (e.g., record data, historical data, etc.). The scoring for each condition may be used to quantify likelihoods that the dependent user has certain abnormal conditions. For example, a certain abnormal condition may be included in an exposure evaluation, which may or may not be a diagnosis, when a numerical score meets or exceeds 90 points. Thus, 90 points may be a maximum threshold. In this example, conditions X and Y are determined to be present and they have numerical scores of 30 and 60, respectively. Thus, a total score of 90 has been determined. Based on this, the exposure evaluation engine 922 can include the certain abnormal condition in the exposure evaluation 1002.

Because the evaluation rules are associated with abnormal conditions, the exposure evaluation engine 922 evaluates the input data (i.e., the unstructured data 1004 and/or the structured data 1006) on a condition-by-condition basis in order to generate the exposure evaluation 1002. In some examples, the exposure evaluation engine 922 initially evaluates those abnormal conditions that the dependent user presents a higher risk for, and then evaluates other less critical abnormal conditions. The exposure evaluation engine 922 may analyze one or more abnormal conditions simultaneously (e.g., in parallel) or in serial. In any event, the evaluation may be structured such that classes of abnormal conditions may be eliminated or not even evaluated when elimination or presence of a certain abnormal condition affects others (e.g., rules them out of consideration).

Thus, the exposure evaluation 1002 is generated on a per abnormal condition basis. In some examples, the exposure evaluation 1002 includes a listing of all the abnormal conditions that were analyzed, including a numerical score for each compared to a threshold score for each.

In some examples, the numerical score can be used to determine likelihood that the dependent user has the abnormal condition. Whether as a straight numerical score or likelihood, an operator or authorized user can evaluate the list and decide whether further follow up with the dependent user would be helpful.

In some examples, the exposure evaluation 1002 includes a minimum amount of information to enable one of the receiving users 904 (e.g., an authorized user) to see who the dependent user is (e.g., John Doe), what abnormal condition may be present (e.g., sepsis), a summary of what prompted the exposure evaluation 1002 (e.g., the structured data 1006 and the unstructured data 1004 and/or the conditions that the exposure evaluation engine 922 identified), a criticality score for the abnormal condition (e.g., based on the abnormal condition and the conditions, how critical is the exposure evaluation), which may correspond to a range of scores, progression rate (e.g., how the abnormal condition is likely to progress), and any other suitable information.

In some examples, the exposure evaluation 1002 is provided to the receiving users 904 via the user interfaces 906 in the form of a notification. The receiving users 904 interact with the exposure evaluation engine 922 via the user interfaces 906. Such interactions include, for example, requesting additional information relating to the exposure evaluation 1002, updating information within the abnormal condition data store 1008, and any other suitable interaction.

Figure 11:
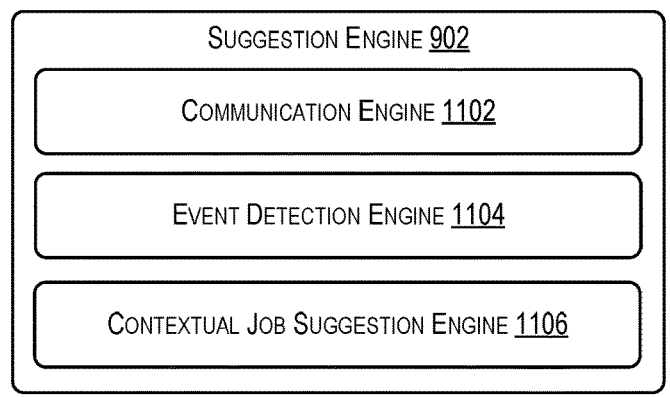
FIG. 11 is an example device which can be used to implement techniques relating to generating contextual suggestions for authorized users as described herein, according to at least one example.

FIG. 11 illustrates an example device 1100 that includes the suggestion engine 902 in accordance with at least one example. The device 1100 may be embodied in software, hardware, and/or firmware. The suggestion engine 902 is configured to manage one or more sub-modules, components, engines, and/or services directed to examples disclosed herein. In some examples, the suggestion engine 902 includes a communication engine 1102, an event detection engine 1104, and a contextual job suggestion engine 1106. While these engines are illustrated in FIG. 11 and will be described as performing discrete tasks with reference to the flow charts, it is understood that FIG. 11 illustrates example configurations and other configurations performing other tasks and/or similar tasks as those described herein may be implemented according to the techniques described herein.

The communication engine 1102 is configured to enable communication with other elements of the environments and networks described herein (e.g., the elements in the environment 900). In some examples, the communication engine 1102 enables communication between other engines of the suggestion engine 902. The communication engine 1102 is also configured to enable communication with one or more components and one or more users. For example, the communication engine 1102 is configured to provide contextual jobs for presentation at a user interface of a component. To do so, the communication engine 1102 may provide suitable instructions to enable the component to render the information about the contextual jobs.

The event detection engine 1104 is configured to access data from elements of the environments and networks described herein. The event detection engine 1104 is also configured to analyze the data from the elements to determine whether an event has taken place (e.g., to detect a particular type of event). The event detection engine 1104 analyzes the data in any suitable manner, which may include analyzing the data in accordance with a set of event detection rules.

The contextual job suggestion engine 1106 is configured to generate jobs based on the event detected and/or any other data accessed by the contextual job suggestion engine 1106 and/or by other engines of the suggestion engine 902. For example, the contextual job suggestion engine 1106 may generate a set of possible jobs, access a profile of an authorized user, access a practice model, access a record of a dependent user, access a dependent user model, and generate a set of contextual jobs. The profile of the authorized user may include a history of events logged by the authorized user. This may include actions taken, outcomes of those actions, and the like. The profile may be compared to a practice model maintained by the contextual job suggestion engine 1106. The practice model can be built using input data from many different authorized users. In some examples, practice model are specific to types of authorized uses (e.g., generalist, specialist type A, specialist type B, etc.). The practice models may also be specific to regions and/or facilities. In any event, the profile of the authorized user may be input into a practice model as part of generating the set of contextual jobs.

A record of the dependent user may be accessed as part of generating the set of contextual jobs. In some examples, the contextual job suggestion engine 1106 accesses only a portion of the record. A dependent user model may also be accessed as part of generating the set of contextual jobs. The dependent user model can be generated from input data from dependent user similar to the dependent user as issue. In some examples, the dependent user model is generated from input data from all dependent users or a randomly selected set of dependent users.

The set of possible jobs include tasks, suggestions, actions, orders, and the like that can be performed and/or authorized by the authorized user. The set of contextual jobs include jobs from the set of possible jobs that are specific to an authorized user who is responsible for a dependent user, specific to authorized users with characteristics similar to those of the authorized user, specific to the dependent user, and/or specific to dependent users with characteristics similar to those of the dependent user. In this manner, the set of contextual jobs may be generated in a manner that considers the context of an attention scenario in which the authorized user is seeing the dependent user. This may include generating jobs in a manner that is considerate of how this authorized user has treated this dependent user and/or similar dependent users and/or in a manner that is considerate of how similar authorized users have treated this dependent user and/or similar dependent users.

Figure 12:
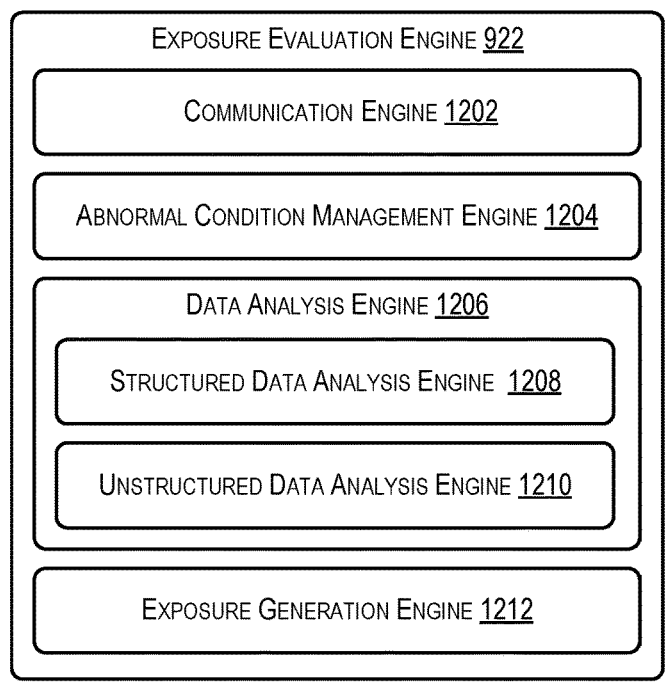
FIG. 12 is an example device which can be used to implement techniques relating to generating context-based evaluations of current conditions as described herein, according to at least one example.

FIG. 12 illustrates an example device 1200 that includes the exposure evaluation engine 922 in accordance with at least one example. The device 1200 may be embodied in software, hardware, and/or firmware. The exposure evaluation engine 922 is configured to manage one or more sub-modules, components, engines, and/or services directed to examples disclosed herein. In some examples, the exposure evaluation engine 922 includes a communication engine 1202, an abnormal condition management engine 1204, a data analysis engine 1206 (including a structured data analysis engine 1208 and an unstructured data analysis engine 1210), and an exposure generation engine 1212. While these engines are illustrated in FIG. 12 and will be described as performing discrete tasks with reference to the flow charts, it is understood that FIG. 12 illustrates example configurations and other configurations performing other tasks and/or similar tasks as those described herein may be implemented according to the techniques described herein.

The communication engine 1202 is configured to enable communication with other elements of the environments and networks described herein (e.g., the elements in the environment 900 including the suggestion engine 902, the transformative processing engine 202, etc.). In some examples, the communication engine 1202 enables communication between other engines of the exposure evaluation engine 922. The communication engine 1202 is also configured to enable communication with one or more components and one or more users. Thus, if an exposure evaluation is generated, the communication engine 1202 determines to whom to send the exposure evaluation (or a notification including the exposure evaluation) and provides for its transport.

The abnormal condition management engine 1204 is configured to manage the lists of abnormal conditions, conditions associated with the abnormal conditions, and the evaluation rules associated with the abnormal conditions and/or conditions. For example, an operator may add a new abnormal condition, conditions, and rules using the abnormal condition management engine 1204. The abnormal condition management engine 1204 is also configured to access data from different elements of the network. In some examples, the communication engine 1202 receives the data and the abnormal condition management engine 1204 accesses portions of the received data that are relevant to one or more abnormal conditions.

The data analysis engine 1206 is configured to monitor, collect, receive, and evaluate data such that an exposure evaluation for a dependent user can later be generated. In particular, the structured data analysis engine 1208 is configured to monitor, collect, receive, and evaluate the data that is in a structured format. This may include data that is objective in nature and which the structured data analysis engine 1208 anticipates receiving. The unstructured data analysis engine 1210 is configured to monitor, collect, receive, and evaluate data that is in an unstructured format. This may include data that is subjective in nature. To this end, as described herein, the unstructured data analysis engine 1210 executes one or more techniques to identify elements (e.g., letters, symbols, numbers, verbs, adjectives, nouns, punctuation, and other parts of speech) of spoken text and/or written text and characteristics of the spoken text and/or written text that may be relevant to their message (e.g., tone, meaning, sarcasm, feelings, inferences, impressions, attitude, outlook, positive/negative/other, and any other characteristic). These techniques include, for example, natural language processing (NLP) using machine learning, Hidden Markov models, Dynamic time warping (DTW), neural networks, deep neural networks and other deep learning models, and any other suitable technique for identifying elements and/or characteristics of spoken text and/or written text.

The data analysis engine 1206 is also configured to evaluate the data to determine whether a particular abnormal condition is present. For example, in order to determine whether a particular condition (of the abnormal condition) is present, the data analysis engine 1206 evaluates data to see if an evaluation rule associated with the condition is fulfilled by the data. Thus, the data analysis engine 1206 evaluates the evaluation rules to determine, not only whether the associated conditions are present, but also to determine whether a suitable number of conditions (or score of one or more conditions) are present to indicate that the associated abnormal condition is present.

The exposure generation engine 1212 is configured to generate exposure evaluations based on output from the data analysis engine 1206. For example, if the data analysis engine 1206 determines that conditions X, Y, and Z are present, and as a result, that abnormal condition A is 75% likely, the exposure generation engine 1212 can generate an exposure evaluation that includes this information. In some examples, the exposure evaluation includes a diagnosis of a particular abnormal condition. The exposure generation engine 1212 is also configured to generate a notification that at least identifies a dependent user and the abnormal condition included in the exposure evaluation. In some examples, the notification includes a subset of data that makes up the exposure evaluation.

FIGS. 13-16 illustrate example flow diagrams showing respective processes 1300, 1400, 1500, and 1600, as described herein. These processes 1300, 1400, 1500, and 1600 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

Figure 13:
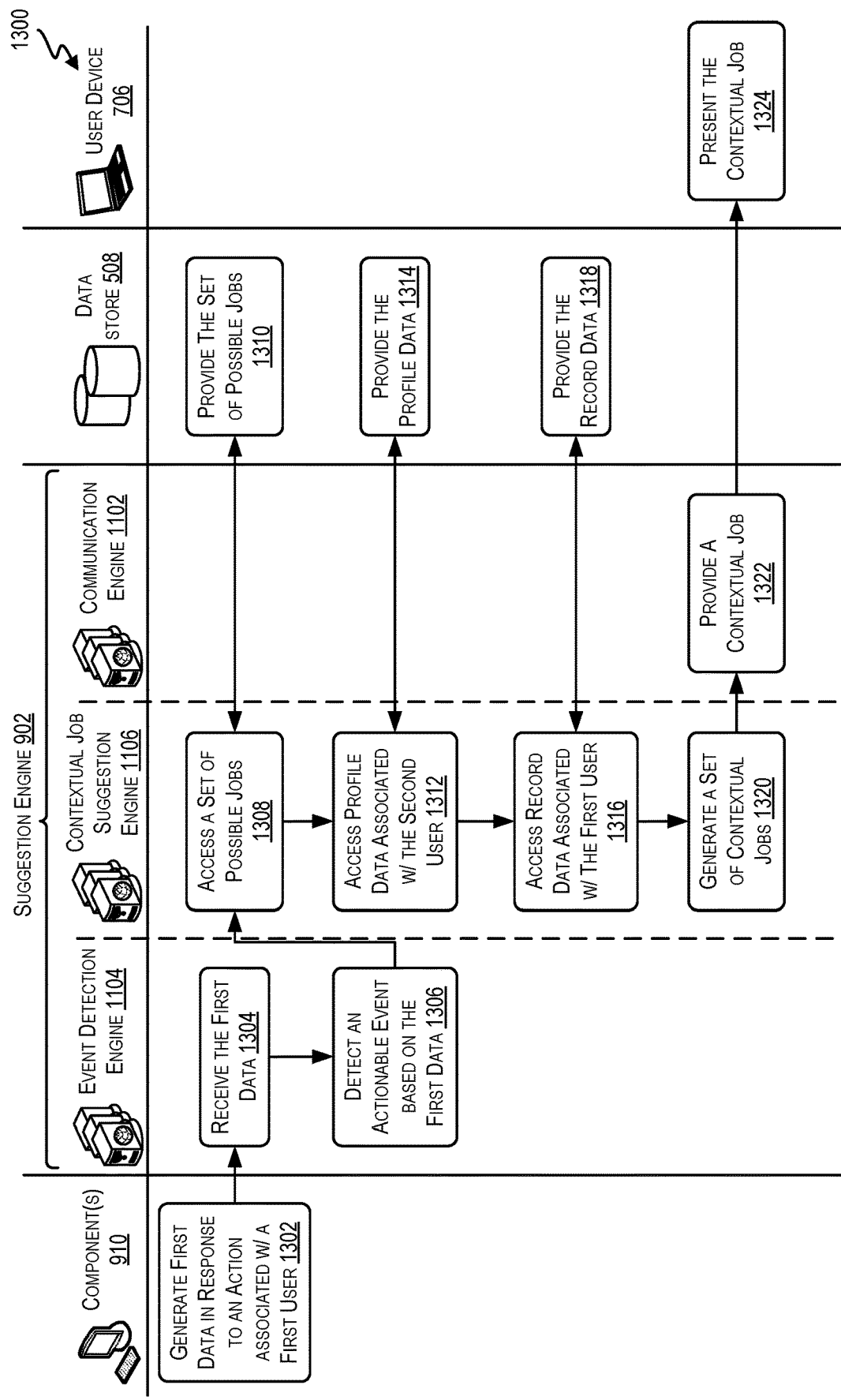
FIG. 13 is a flow diagram depicting example acts for implementing techniques relating to generating contextual suggestions for authorized users as described herein, according to at least one example.

FIG. 13 illustrates a flowchart of the process 1300 for generating contextual jobs according to at least one example. The components 910, the suggestion engine 902, the data store 508, and the user device 706 may perform the process 1300.

The process 1300 begins at 1302 by generating first data in response to an action associated with a first user. This may be performed by the component 910. The first data may be generated automatically by the component 910 and/or in response to user input. For example, the first data may be generated by a machine that runs a test on the first user and outputs results of the test as the first data. The first data may also be generated by a second user using a user device to make a record entry to a record associated with the first user. The action may include an action taken by the second user as part of addressing current conditions of the first user. These conditions may include health conditions. In some examples, the component 910 is a data store and the first data is generated as the first data is saved in the data store.

At 1304, the process 1300 receives the first data. This may be performed by the event detection engine 1104 of the suggestion engine 902. The first data may be received via a messaging bus and/or via an agent executing in the component 910.

At 1306, the process 1300 detects an actionable event based on the first data. This may be performed by the event detection engine 1104. The actionable event may be a type of event that prompts further action by the suggestion engine 902. For example, the action associated with the first user may be a first type of action that does not constitute an actionable event, and therefore does not require further action by the suggestion engine 902 (e.g., generation of the contextual jobs). Such actions are typically minor in nature and are not suggestive of the second user addressing current conditions in a meaningful way. The action may constitute an actionable event when the first data indicates that the action is suggestive of the second user addressing current conditions in a meaningful way. For example, if the first data indicates that the second user has placed an order, input a diagnosis, or performed some other major action with respect to the first user, the action may be considered an actionable event. The detection of an actionable event will result in the suggestion engine 902 performing additional operations to identify contextual jobs that can be suggested to the second user, which may be related to the earlier action associated with the first user.

At 1308, the process 1300 accesses a set of possible jobs. This may be performed by the contextual job suggestion engine 1106 of the suggestion engine 902. The set of possible jobs may correspond to the addressing the current conditions of the first user. In some examples, the set of possible jobs includes a superset of jobs relating to the action and/or the actionable event. In some examples, the set of possible jobs may have been previously generated and associated with the action and/or the actionable event. In this manner, the set of possible jobs may be generic with respect to the first user and/or the second user.

Accessing the set of possible jobs at 1308 may include accessing the data store 508 to retrieve the set of possible jobs at 1310. In other words, the set of possible jobs may be stored in the data store 508 or any other comparable data structure, and provided by the data store 508.

At 1312, the process 1300 accesses profile data associated with the second user. This may be performed by the contextual job suggestion engine 1106. For example, the profile data may be associated with a profile (e.g., a practice profile) of the second user. The profile data may include historical practice data, demographic data, location data, preference data, and the like of the second user. In this manner, contextual jobs may be generated in a manner that considers the context as it relates to the second user. In some examples, the profile data is associated with other users similar to the second user. In this manner, contextual jobs may be generated in a manner that considers the context as it relates to other users similar to the second user.

Accessing the profile data associated with the second user at 1312 may include accessing the data store 508 to retrieve the profile data at 1314. Thus, the profile data may be stored in the data store 508 and/or within any other comparable data structure, and provided by the data store 508.

At 1316, the process 1300 accesses record data associated with the first user. This may be performed by the contextual job suggestion engine 1106. For example, the record data may be associated with one or more records that store data about the first user. In some examples, the record data is associated with a profile (e.g., a treatment profile) of the first user. In any event, the record data may include historical treatment data, demographic data, record data, preference data, and the like. In this manner, contextual jobs may be generated in a manner that considers the context as it relates to the first user. In some examples, the record data is associated with other users similar to the first user. In this manner, contextual jobs may be generated in a manner that considers the context as it relates to other users similar to the first user.

Accessing the record data associated with the first user at 1316 may include accessing the data store 508 to retrieve the record data at 1318. Thus, the record data may be stored in the data store 508 and/or within any other comparable data structure, and provided by the data store 508.

At 1320, the process 1300 generates a set of contextual jobs. This may be performed by the contextual job suggestion engine 1106. Generating the set of contextual jobs may be based on the set of possible jobs, the profile data, and/or the record data. In some examples, the set of contextual jobs includes a subset of the set of possible jobs that is particularized to the first user and/or the second user. In some examples, the set of contextual jobs include actions that may be taken by the second user that are related to addressing the current conditions of the first user. Each job of the set of contextual jobs may be assigned one or more scores (e.g., a relevancy score, a criticality score, etc.). These scores may be used to rank or otherwise organize the set of contextual jobs. The scores may be computed based on score rules that identify interrelationships between the presence of certain data and suggestions.

At 1322, the process 1300 provides a contextual job. This may be performed by the communication engine 1102 of the suggestion engine 902. The contextual job may be one of the set of contextual jobs generated at 1320. The contextual job is provided in any suitable manner. The full set of contextual jobs may also be provided. In some examples, providing the contextual job includes formatting the contextual job to be presentable in an existing workflow of the second user. For example, the contextual job may be sent to a practice management application, and presented by the practice management application (e.g., see 1324). In some examples, providing the contextual job is based on the scores assigned to the contextual job.

At 1324, the process 1300 presents the contextual job. This may be performed by the user device 709. For example, the contextual job may be provided to the user interface 906, which may be presented on the user device 706. In some examples, presenting the contextual job may include making adjustments to the contextual job to ensure that the contextual job is displayed appropriately. In some examples, presenting the contextual job is based on the scores assigned to the contextual job. Presenting the contextual job may be considerate of the importance of the contextual job with respect to other contextual jobs and/or other information presented.

Figure 14:
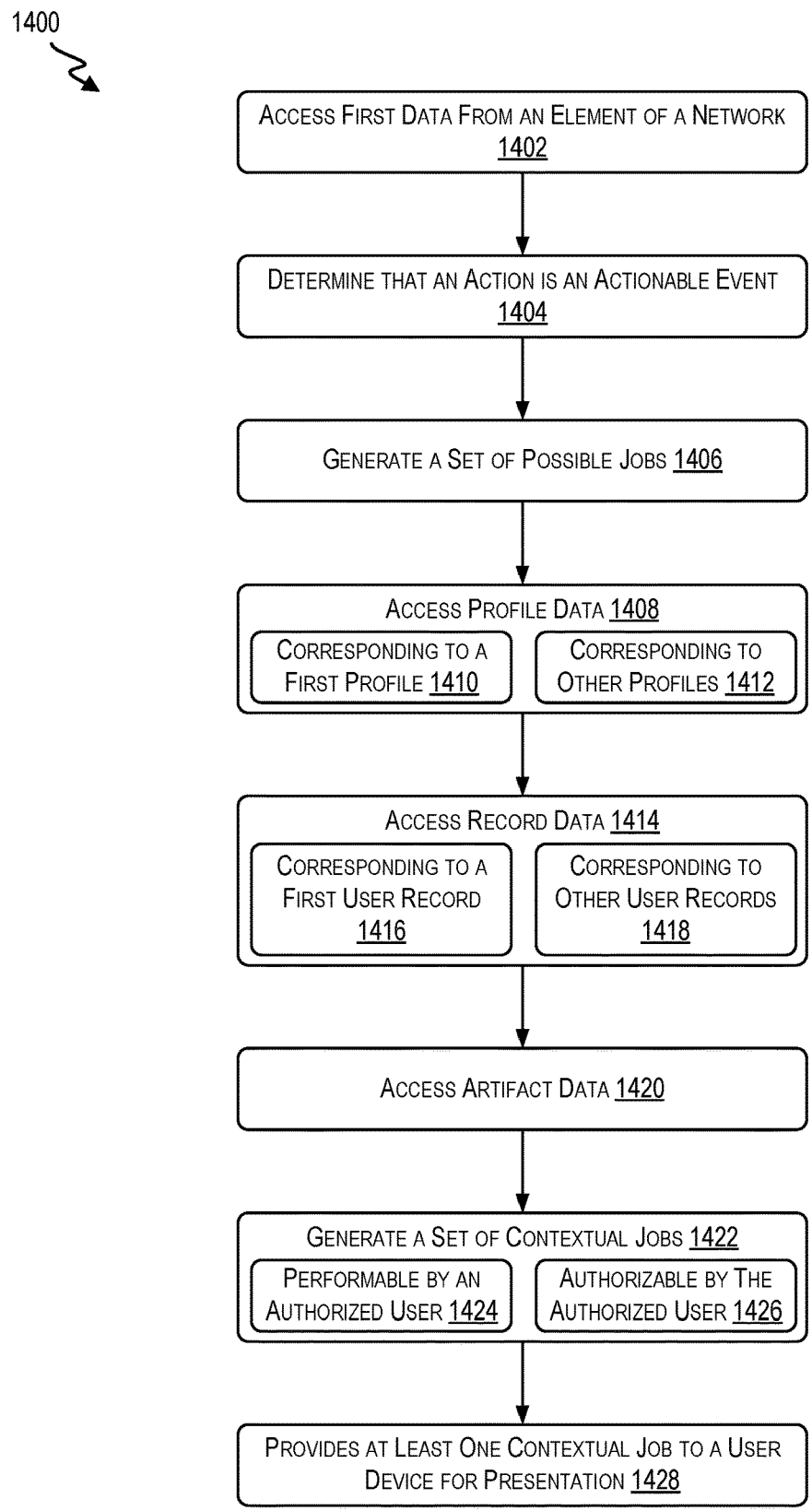
FIG. 14 is a flow diagram depicting example acts for implementing techniques relating to generating contextual suggestions for authorized users as described herein, according to at least one example.

FIG. 14 illustrates a flowchart of the process 1400 for generating contextual jobs according to at least one example. The suggestion engine 902 may perform the process 1400. The process 1400 begins at 1402 by accessing first data from an element of a network. This may be performed by the event detection engine 1104. In some examples, the first data is generated in response to an action performed by an authorized user and relating to a dependent user. The authorized user may be authorized to attend to the dependent user to address current conditions of the dependent user. The element of the network may include an electronic record system that stores user records and enables authorized users to edit the user records, an integrated record system that enables sharing of the user records, an active enterprise data warehouse comprising multiple different types of data, a diagnostic device, a diagnostic machine capable of performing one or more tests on the dependent user, a user device, a sensor device capable of sensing conditions relating to the dependent user, and/or any other suitable component or element.

At 1404, the process 1400 determines that an action of the authorized user is an actionable event. This may be performed by the event detection engine 1104. Determining that the action is an actionable event is based on the first data. The actionable event includes at least one of an ordering event, a decision point event, an escalation event, or a communication event. In some examples, the action performed by the authorized includes one or more adjustments to a record associated with the dependent user.

At 1406, the process 1400 generates a set of possible jobs. This may be performed by the contextual job suggestion engine 1106. Generating the set of possible jobs is based on the actionable event and/or relate to the actionable event. The set of possible jobs correspond to addressing the current conditions of the dependent user.

At 1408, the process 1400 accesses profile data. This may be performed by the contextual job suggestion engine 1106. The profile data may correspond to a first profile 1410 or may correspond to other profiles 1412. For example, the first profile may be a profile of the authorized user. In this example, the first profile includes historical action data and first user data of the authorized user. The other profiles may correspond to other authorized users and include similar historical action data and user data of the other authorized users. The historical record data may include structured data and unstructured data that describes aspects of historical interactions between at least one of the user and the authorized user or the dependent user and other authorized users. In some examples, the historical data includes data describing interactions of the authorized user with possible jobs of a set of possible jobs with respect to other dependent users.

At 1414, the process 1400 accesses record data. This may be performed by the contextual job suggestion engine 1106. The record data may correspond to a first user record 1416 or may correspond to other user records 1418. For example, the first user record may be a record of the dependent user. In this example, the first user record includes historical record data of the dependent user and second user data of the dependent user. The other records may correspond to other dependent users and include similar other historical record data and other second user data of the other dependent users.

At 1420, the process 1400 accesses artifact data (e.g., knowledge artifacts). This may be performed by the contextual job suggestion engine 1106. The artifact data is descriptive of conditions of other dependent users that are similar to the current conditions of the dependent user.

At 1422, the process 1400 generates a set of contextual jobs. This may be performed by the contextual job suggestion engine 1106. Generating the set of contextual jobs may be based on the set of possible jobs, the first profile, the other profiles, the first user record, the other user records, and/or the artifact data. The set of contextual jobs may include a first contextual job that is performable by the authorized user and which corresponds to addressing the current conditions of the dependent user 1424 and/or a second contextual job that is authorizable by the authorized user, performable by a different authorized user, and which corresponds to addressing the current conditions of the dependent user 1426.

At 1428, the process 1400 provides at least one contextual job from the set of contextual jobs to a user device for presentation. This may be performed by the communication engine 1102. The user device may be associated with the authorized user. In some examples, providing at least one contextual job to the user device for presentation includes providing the set of contextual jobs to the user device for presentation at the user device in accordance with a presentation rule. In some examples, each contextual job of the set of contextual jobs is defined by at least one of a criticality score, a relevance score, or an availability score. The presentation rule may indicate how to present the set of contextual jobs based on the score(s). For example, the presentation rule may include a set of conditional statements.

The process 1400 may further include generating an evaluation for the dependent user based on record data corresponding to a record of the dependent user. The evaluation may indicate a prospect that the dependent user has an abnormal condition that is related to the current conditions. In this example, generating the set of contextual jobs is further based on the evaluation.

Figure 15:
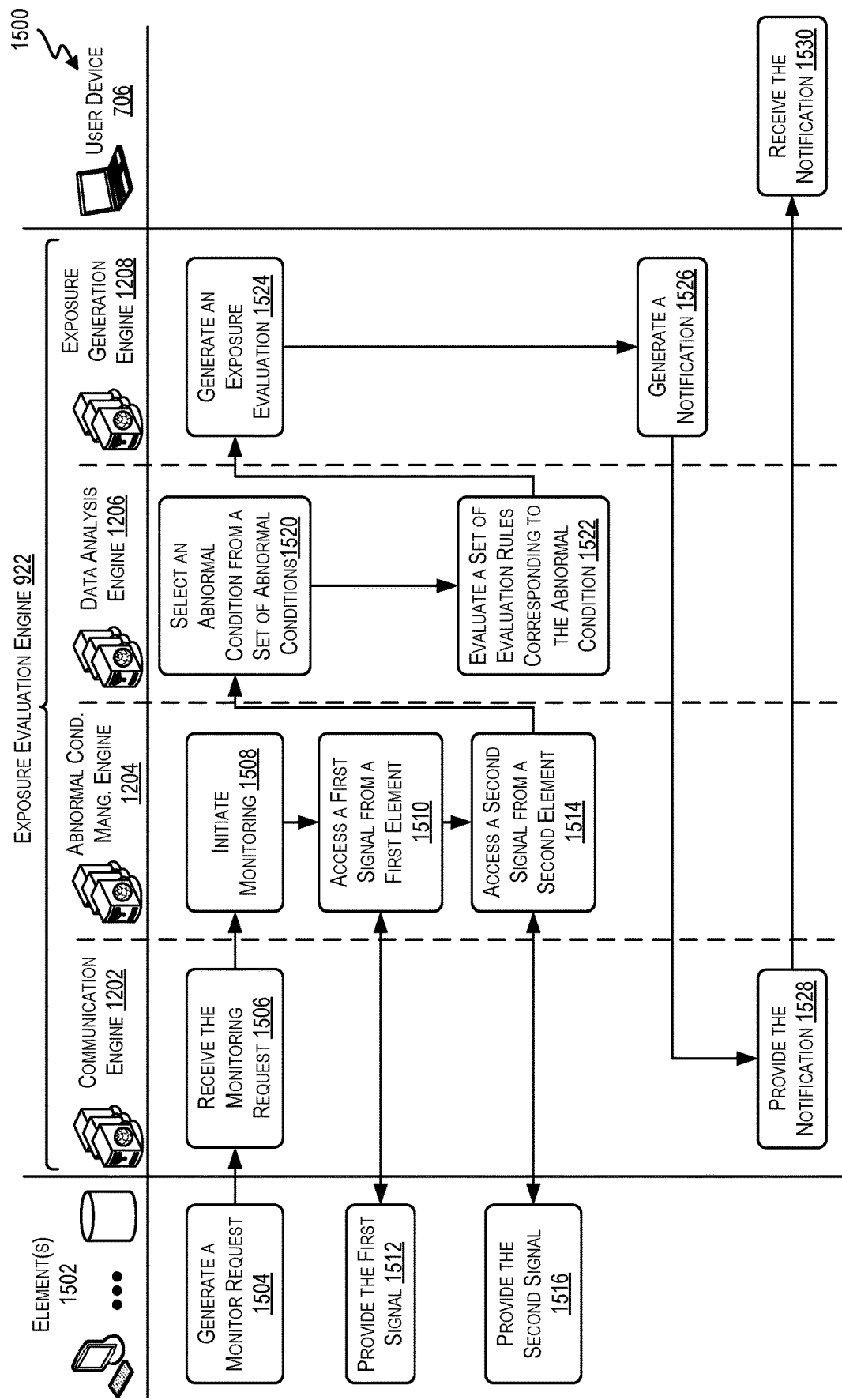
FIG. 15 is a flow diagram depicting example acts for implementing techniques relating to generating context-based evaluations of current conditions as described herein, according to at least one example.

FIG. 15 illustrates a flowchart of the process 1500 for generating exposure evaluations according to at least one example. Elements 1502 (e.g., the components 910, the transformative processing engine 202, etc.), the exposure evaluation engine 922, and the user device 706 may perform the process 1500. In some examples, at least a portion of the process 1500 runs continuously as users are treated at different facilities. In this manner, the process 1500 may predict certain abnormal conditions that the users may be at risk for. These predictions can be made even as authorized users are responding to current conditions of other users and/or the users for which the process 1500 is working.

The process 1500 begins at 1504 by generating a monitoring request. This may be performed by one of the elements 1502. For example, a user device may generate the monitoring request in response to user input that indicates a first user's desire that the monitoring request be generated. The monitoring request may identify the first user and one or more abnormal conditions to be monitored. In some examples, the first user may have previously granted permission to a second user to request the monitoring request. In some examples, monitoring may be a condition of treatment of the first user by the second user.

At 1506, the process 1500 receives the monitoring request. This may be performed by the communication engine 1202 of the exposure evaluation engine 922. The monitoring request is received from the element 1502.

At 1508, the process 1500 initiates monitoring. This may be performed by the abnormal condition management engine 1204 of the exposure evaluation engine 922. Initiating monitoring may include sending instructions to monitoring agents associated with elements (e.g., the elements 1502). The instructions may identify the user and/or a user record by a user identifier or other unique identifier. The instructions may also identify one or more abnormal conditions by unique abnormal condition identifiers. The monitoring agents may use the user identifiers and the abnormal condition identifiers to identify signals generated and/or processed by the elements 1502 to collect and send to the exposure evaluation engine 922. In some examples, initiating monitoring may include sending a subscription request to a messaging bus to collect data that identifies and first user, the abnormal condition(s), and any other suitable information.

At 1510, the process 1500 access a first signal (e.g., first data) from a first element. This may be performed by the abnormal condition management engine 1204. Accessing the first signal may include receiving the first signal in response to a request for the first signal. In some examples, accessing the first signal may include receiving the signal without first requesting the first signal. The first signal may be associated with the user and/or the abnormal condition. For example, the first signal may be output from a user device (e.g., a first element) that is processing a test associated with the user. In some examples, the first signal includes geographic data accessed from a social media platform (e.g., Facebook, Instagram, Twitter, Snapchat, etc.). For example, the first signal my represent Facebook posts and/or comments of users located in Florida that identify a particular abnormal condition. In some examples, the geographic region may be smaller than or larger than a state. For example, the first signal may represent Twitter posts of users located in Orlando that identify the particular abnormal condition and/or other factors that may contribute to the abnormal condition. For example, assume that the abnormal condition is Measles; the first signal may represent online discussions about Measles in a particular area. In some examples, the first signal may include a feed from a government notification system. For example, the government notification system may notify sub scribed users of outbreaks of certain diseases and the like. This signal may be used to generate the exposure evaluations described herein.

Accessing the first signal from the first element at 1510 may include accessing the element(s) 1502 to retrieve the signal data at 1512. Thus, the first signal may originate and/or be processed by the elements 1502 and/or provided to the abnormal condition management engine 1204.

At 1514, the process 1500 accesses a second signal from a second element. This may be performed by the abnormal condition management engine 1204. Accessing the second signal may include receiving the second signal in response to a request for the second signal. In some examples, accessing the second signal may include receiving the second signal without first requesting the second signal. Like the first signal, the second signal may be associated with the first user and/or the abnormal condition(s). In this manner, the second signal may be relevant to generating the exposure evaluations that reference the user and the abnormal condition(s). For example, the second signal may include updated vital sign data accessed from a data store (e.g., a second element) that stores a record of the first user.

Accessing the second signal from the second element at 1514 may include accessing the element(s) 1502 to retrieve the signal data at 1516. Thus, the second signal may originate and/or be processed by the elements 1502 and/or provided to the abnormal condition management engine 1204.

At 1520, the process 1500 selects an abnormal condition from a set of abnormal conditions. This may be performed by the data analysis engine 1206. Selecting the abnormal condition from the set of abnormal conditions may include selecting the abnormal condition based on the first signal and the second signal. In some examples, selecting the abnormal condition includes selecting the abnormal condition based on the monitoring request. For example, the monitoring request may identify the abnormal condition. In some examples, the monitoring request is a generic monitoring request that may not specifically identify any one particular abnormal condition. In this example, selecting the abnormal condition may be based on criticality and/or relevance of the abnormal conditions with respect to the first user. For example, when the exposure evaluation engine 922 has access to data that indicates that the first user is located within a facility that has a high risk of sepsis outbreaks, sepsis may be the first abnormal condition selected from the set of abnormal conditions. This is because the first user being located at the facility may be at a risk of developing sepsis.

At 1522, the process 1500 evaluates a set of evaluation rules corresponding to the abnormal condition. This may be performed by the data analysis engine 1206. Evaluating the set of evaluation rules may be based on the first signal, the second signal, and other signals received from other elements. For example, the data analysis engine 1206 may use the signals as inputs to an algorithm that references the evaluation rules. Output from the algorithm may include information that can be used by the exposure generation engine 1212 to generate the exposure evaluation at 1524. The output may represent which conditions of which rules were met during the evaluation. For some complex abnormal conditions, the number of evaluation rules may be very high. This may be because many different factors could affect whether or not the first user has the abnormal condition. The output may be expressed as a set of binary values indicating whether the input signals fulfilled the conditions of the evaluation rules. In some examples, the output may be expressed as a percentage (e.g., 10%) or value within a range (e.g., 15 in a range of 1-50). The output, whether expressed as a binary value, a percentage, a value within a range, or otherwise, may be weighted based on the corresponding evaluation rule. For example, certain evaluation rules may be more relevant to certain abnormal conditions than others. Similarly, certain evaluation rules may be related to other evaluations rules such that their combined fulfillment constitutes a heavier weighting than they would be separately. For example, assume that a first evaluation rule has a weighting of 0.2 and a second evaluation rule has a weighting of 0.3. A third evaluation rule may indicate that when the first evaluation rule and the second evaluation rules are both met, the weighting of both should be increased by 0.1.

At 1524, the process 1500 generates an exposure evaluation. This may be performed by the exposure generation engine 1212 of the exposure evaluation engine 922. Generating the exposure evaluation may include using output from block 1522 to generate an exposure score. The exposure score may be represented in any suitable manner (e.g., a binary value, a percentage, a value within a range, a text string, etc.) and may include multiple parts. In some examples, the exposure score may indicate that the first user has the abnormal condition and/or a risk that the first user will contract the abnormal condition. For example, the exposure score may include a binary value (e.g., 0) indicating that the first user does not have the abnormal condition, but may also include a percentage (e.g., 60%) indicating a likelihood that the first user will get the abnormal condition within some period of time. The period of time may be fixed based on a period (e.g., next two weeks), fixed based on an event (e.g., during the time the first user will be present in a facility), indefinite, variable, or have any other suitable characteristic. The exposure evaluation may be prepared for evaluation by second users authorized to attend to the first users. In some examples, the exposure evaluation may be persisted to a database that stores exposure evaluations. In other examples, the exposure evaluations may be stored for some period and then erased.

At 1526, the process 1500 generates a notification. This may be performed by the exposure generation engine 1212. The notification may be used to carry the exposure evaluation. For example, the notification may be a document that includes the data from the exposure evaluation. The notification may be any suitable message formatted according to any suitable standard. For example, the notification may comply with the HL7 standard. In some examples, generating the notification may include generating multiple notifications for delivery to different users using different applications and/or devices. For example, a first notification may be generated for a second user who is keenly familiar with the current conditions of the first user. This notification may be formatted for delivery to a practice management system where the second user can access a record corresponding to the first user. A second notification may be generated for a third user who is responsible for managing the spread of abnormal conditions within a facility. This notification may be formatted for delivery to a station within the facility where the third user can access the second notification.

At 1528, the process 1500 provides the notification. This may be performed by the communication engine 1202. Providing the notification may include selecting a destination device, application, etc. and sending the notification.

At 1530, the process 1500 receives the notification. This may be performed by the user device 706. The notification may also be sent to other elements, as described herein. The user device 706 may be configured to present the notification in any suitable manner.

Figure 16:
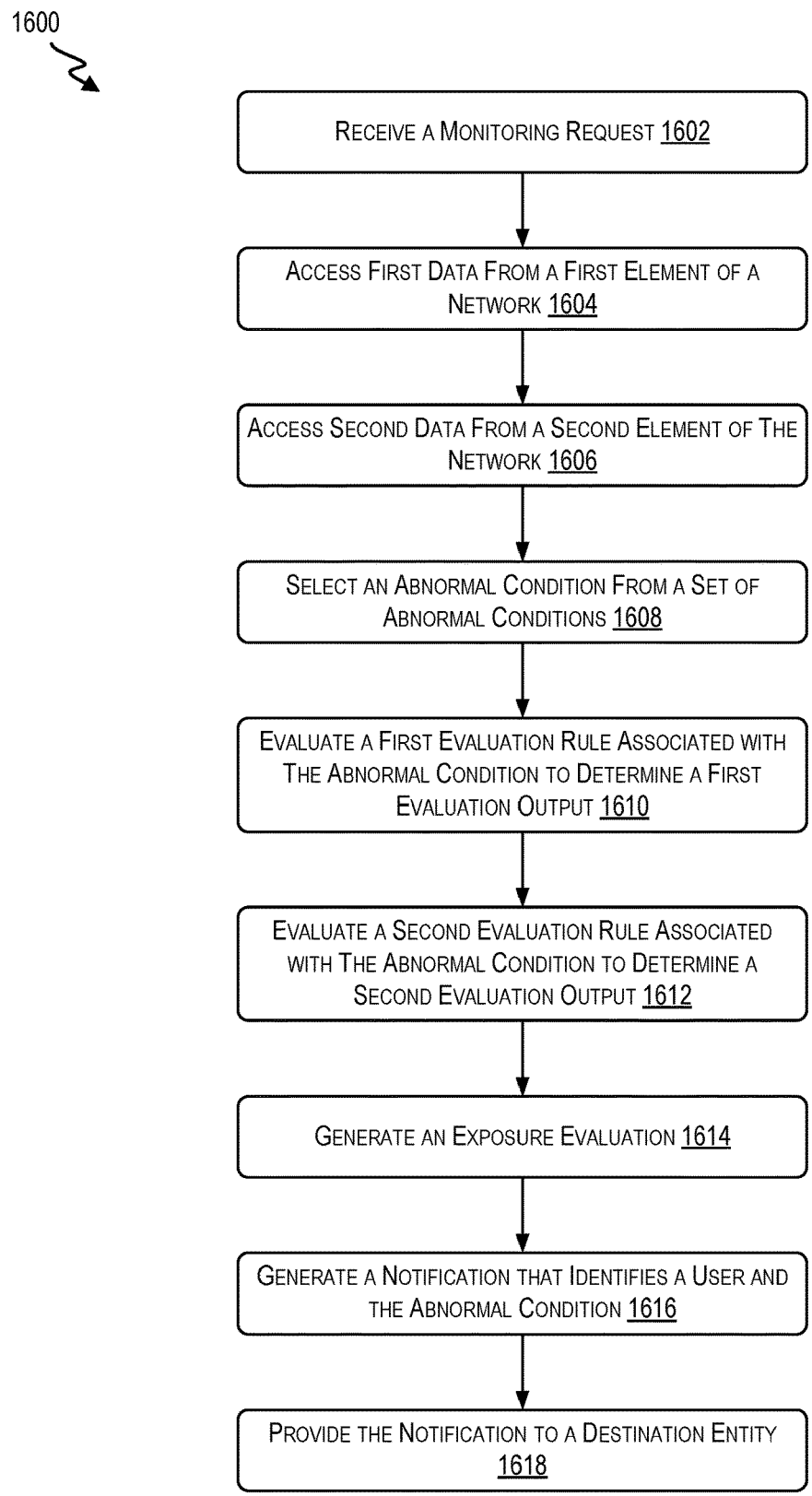
FIG. 16 is a flow diagram depicting example acts for implementing techniques relating to generating context-based evaluations of current conditions as described herein, according to at least one example.

FIG. 16 illustrates a flowchart of the process 1600 for generating exposure evaluations according to at least one example. The exposure evaluation engine 922 may perform the process 1600. The process 1600 begins at 1602 by receiving a monitoring request identifying a user. This may be performed by the communication engine 1202. The monitoring request requests monitoring of data corresponding to the user and generation of an exposure evaluation for the user based on the monitoring. The exposure evaluation indicates at least one of a possibility of the user having an abnormal condition or a possibility of the user developing the abnormal condition.

At 1604, the process 1600 accesses first data from a first element of a network. This may be performed by the abnormal condition management engine 1204. In some examples, at least a portion of the first data corresponds to the user and includes one or more objective values corresponding to the user.

At 1606, the process 1600 accesses second data from a second element of the network. This may be performed by the abnormal condition management engine 1204. In some examples, at least a portion of second data corresponds to the user and includes one or more subjective observations corresponding to the user.

In some examples, the first element and the second element each comprise at least one of an electronic record system that stores user records and enables authorized users to edit the user records, an integrated record system that enables sharing of the user records, an active enterprise data warehouse comprising multiple different types of data, a diagnostic device, a diagnostic machine capable of performing one or more tests on the user, a user device, or a sensor device capable of sensing conditions relating to the user.

In some examples, the first element and/or the second element include monitoring agents. The process 1600 may further include prior to accessing the first data and/or the second data, instructing, based on the monitoring request, the monitoring agents to: monitor data defined by a data attribute corresponding to the first data and/or the second data, identify the first data and/or the second data based on the monitored data, and provide the first data and/or the second data for use in generating the exposure evaluation.

In some examples, the user is a dependent user associated with an authorized user who is authorized to address current conditions of the dependent user. The first data and/or the second data can be generated in connection with the authorized user who, in responding to one or more conditions of the dependent user, makes one or more adjustments to a record associated with the dependent user.

In some examples, the process 1600 further includes receiving a subscription request at a messaging bus that monitors messages that flow across the messaging bus. The subscription request requests data defined by a data attribute corresponding to the first data and/or the second data. In some examples, accessing the first data and/or second data includes receiving the first data and/or the second data from the messaging bus in response to the messaging bus detecting the first data and/or the second data based on the subscription request.

At 1608, the process 1600 selects an abnormal condition from a set of abnormal conditions. This may be performed by the data analysis engine 1206. In some examples, the abnormal condition is associated with one or more evaluation rules. Each evaluation rule of the one or more evaluation rules indicates a condition corresponding to at least one of an absence of the abnormal condition or a presence of the abnormal condition. In some examples, selecting the abnormal condition from the set of abnormal conditions is based on the portion of the first data and/or the portion of the second data.

At 1610, the process 1600 evaluates a first evaluation rule associated with the abnormal condition to determine a first evaluation output. This may be performed by the data analysis engine 1206. In some examples, evaluating the first evaluation rule includes using the first data or the second data as input. The first evaluation output indicates whether the first data or the second data fulfills a first condition of the first evaluation rule.

At 1612, the process 1600 evaluates a second evaluation rule associated with the abnormal condition to determine a second evaluation output. This may be performed by the data analysis engine 1206. In some examples, evaluating the second evaluation rule includes using the first data or the second data as second input. The second evaluation output indicates whether the first data or the second data fulfills a second condition of the second evaluation rule.

In some examples, the process 1600 further includes accessing third data from a third element of the network. At least a portion of the third data includes geographic data that corresponds to the abnormal condition. For example, the geographic data may indicate the spread of the abnormal condition in a particular geographic region. The process 1600 may further include evaluating a third evaluation rule associated with the abnormal condition to determine a third evaluation output. The third data may be used as input to a third second evaluation rule associated with the abnormal condition to determine a third evaluation output. The third evaluation output indicates whether the third data fulfills a first condition of the third evaluation rule. In some examples, determining the exposure evaluation for the user is further based on the third evaluation output.

At 1614, the process 1600 generates an exposure evaluation. This may be performed by the exposure generation engine 1212. In some examples, generating the exposure evaluation is based on the first evaluation output and/or the second evaluation output. The exposure evaluation may be for the user. In some examples, generating the exposure evaluation includes generating an exposure score that indicates at least one of the possibility of the user having the abnormal condition or the possibility of the user developing the abnormal condition, and generating the exposure evaluation when the exposure score falls within a threshold. Comparing the exposure score to the threshold may ensure that computing resources used to generate exposure evaluations are dedicated to only generating exposure evaluations for those abnormal conditions that are likely to be relevant to the user.

At 1616, the process 1600 generates a notification that at least identifies the user and the abnormal condition. This may be performed by the exposure generation engine 1212. In some examples, generating the notification is based on the exposure evaluation. In some examples, the notification is a first notification formatted for a first destination entity and include a first payload. The process 1600 further includes generating, based on the exposure evaluation, a second notification formatted for a second destination entity and including a second payload.

At 1618, the process 1600 provides the notification to a destination entity. This may be performed by the communication engine 1202. In some examples, the destination entity may be determined based on the exposure score. For example, scores indicating higher criticality and/or relevancy to a user may be sent in a first obtrusive notification, while scores indicating lower criticality and/or relevancy may be sent in a second less obtrusive notification. In some examples, the destination entity includes at least one a first computing device executing a user attention management application associated with a first authorized user who is authorized to attend to the user, a mobile device executing a mobile user attention management application associated with the first authorized user, or a second computing device executing a user population management application associated with a second authorized user who is authorized to manage the spread of the abnormal condition within a user population.

In some examples, the process 1600 further includes accessing the exposure evaluation and generating a suggestion notification based on the exposure evaluation. The suggestion notification includes a set of suggestions for consideration by an authorized user as part of responding to the abnormal condition of the user. The process 1600 further includes determining a destination entity associated with the authorized user, and providing the suggestion notification to the destination entity.

Examples of the disclosure provide for a number of technical advantages. For example, the disclosure enables efficient evaluation of real-time data to provide timely and relevant contextual jobs for authorized users. Because the contextual jobs are timely and relevant, an authorized user is likely to perform a greater percentage of the contextual jobs as compared to other approaches that provide only generic recommendations. This results in improved attention for a dependent user whom the authorized user is evaluating. In addition, the contextual jobs can be tailored over time to correspond to the way the authorized user interacts in certain situations. In this manner, the contextual jobs are not only relevant to the user, but, in a way, begin to predict likely actions of the authorized user given a certain set of facts. Not only can the model be used to generate contextual jobs, in some examples, it may also be used to compare authorized users for make suggestions for improved processes. These suggestions can be based on extensive data sets gathered from many authorized users in ways that existing systems have not comprehended. Additionally, the manner in which the contextual jobs are presented provides a technical advantage as compared to conventional approaches.

Additional, the manner in which the contextual jobs are presented to authorized users provides a technical advantage and avoids alarm fatigue caused by too many notifications. Instead, more relevant and/or critical jobs are presented in a more obtrusive manner, while less relevant and/or less critical jobs are presented in a less obtrusive manner. This ensures better adoption and use of contextual jobs.

The examples of this disclosure also provide other technical advantages. For example, exposure evaluations may be generated based on data collected from a multitude of different systems. These systems output data in various formats, at various intervals, and the like. Nevertheless, this output data can be processed, weighted, and used to make predictions included in the exposure evaluations. The exposure evaluations can be formatted on the fly for appropriate presentation at different destination entities. This enables the exposure evaluations to seamlessly be integrated into existing process flows.

Figure 17:
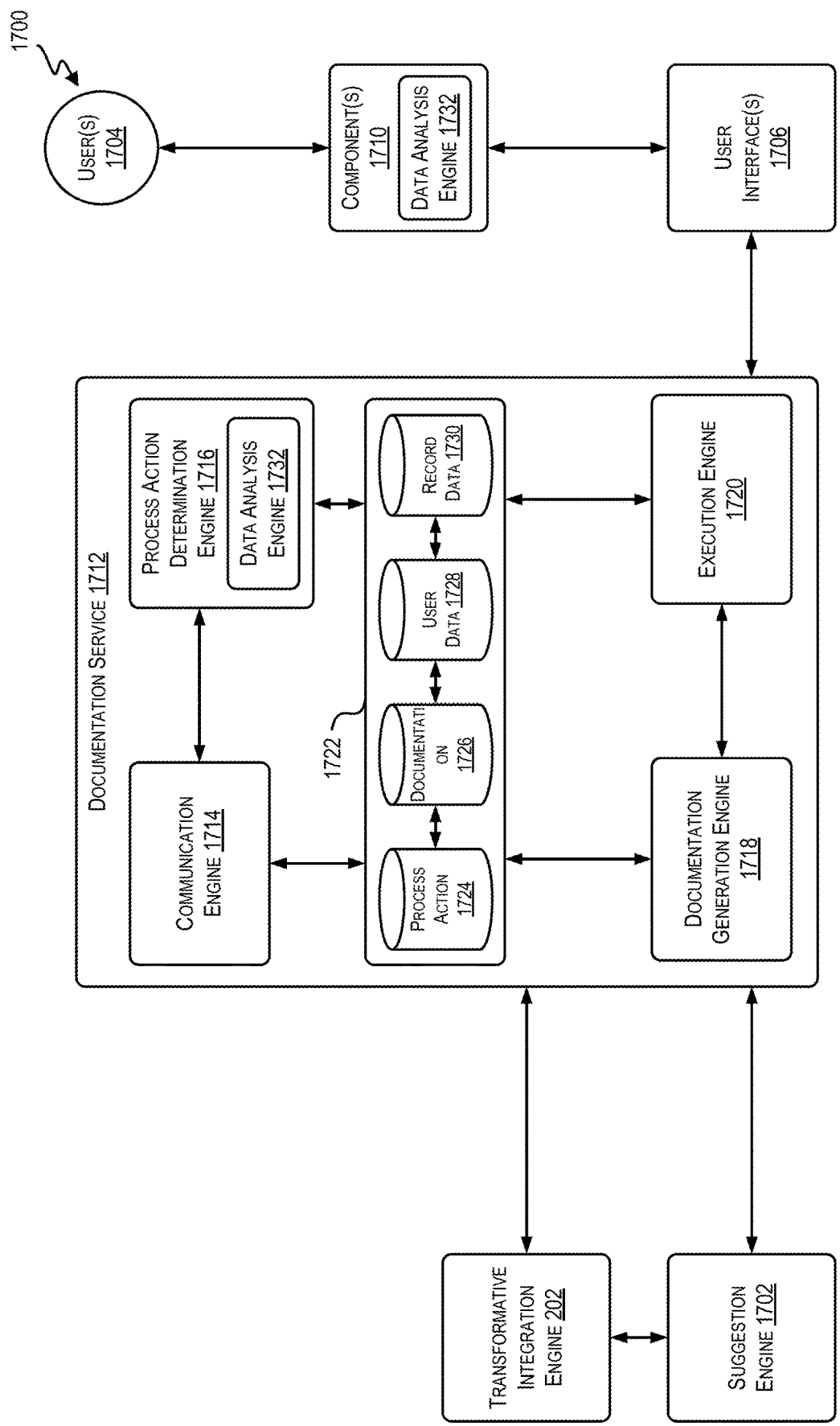
FIG. 17 is an example block diagram illustrating an environment in which techniques relating to determining process actions based on documentation as described herein may be implemented, according to at least one example.

Turning now to FIG. 17, an interaction system 1700 is shown according to at least one example. The interaction system 1700 may be implemented using at least some of the elements of the interaction system 800. In this manner, the interaction system 1700 may include computer devices communicatively coupled via one or more communications network. The interaction system 1700 includes a documentation service 1712, the transformative processing engine 202, and a suggestion engine 1702. The documentation service 1712 is configured to implement techniques relating to generating future process actions and otherwise managing documentation, as described herein. For example, the documentation service 1712 can provide a user interface for professional users (e.g., medical professionals) to input documentation about a dependent user (e.g., a patient, a customer, a consumer, a potential patient, a former patient, etc.); determine, based on the documentation, whether certain future process actions have been or should be placed; determine, based on past or future process actions, whether a record associated with the dependent user has sufficient documentation to support a past process action or a future process action; and reconcile any discrepancies between process actions, supporting documentation, and problem lists associated with the dependent user.

To this end, the documentation service 1712 receives information from any of a variety of elements of the interaction system 1700. For example, users 1704 can use components 1710 to interact with the documentation service 1712. The users 1704 are examples of professional users and the components 1710, in some examples, are examples of computing devices by which the users 1704 can input documentation describing dependent users. In some examples, the documentation service 1712 provides one or more user interfaces 1706 that can be presented at the components 1710. For example, the documentation described herein can be input by the users 1704 at the user interfaces 1706. In some examples, the user interfaces 1706 include graphical user interfaces, application programming interfaces, or other interfaces to enable exchange of information between the components 1710 and the documentation service 1712. In some examples, the components 1710 are communicatively coupled to the document service 1712 via any suitable network connection.

The documentation service 1712 may interact using the active unified data layer 308, the access management layer 310, the interface layer 316, and/or the application device layer 320. In some examples, at least a portion of the interactions of the documentation service 1712 take place in the interface layer 316 and/or the application/device layer 320. In this manner, the documentation service 1712 is configured to process documentation input at the components 1710 (e.g., via the user interfaces 1706 in the interface layer 316 or the application layer 320). The user interfaces 1706 are examples of the user interfaces capable of generation by the interface engine 702 and may be accessed by the user 1704 using applications running on user devices as described herein. The documentation service 1712 provides the suggested process actions to the user interfaces 1706 by sending the process actions in accordance with an earlier subscription and/or by publishing the process actions to a common location, which may be accessed by an application supporting the user interface 1706 (e.g., via one or more application programming interfaces (API) calls).

The users 1704 may come from the same group of users and may be similar to the users that operate the components 410-418 and/or the users that operate the user devices 706-714. Accordingly, the users 1704 interact with components 1710 to generate data, receive data, and otherwise interact with other elements of the interaction system 1700. The components 1710 are examples of the components 410-418 discussed herein.

In some examples, the components 1710 automatically (e.g., without user input) generate certain events that are provided to the documentation service 1712 for further processing. For example, an example component 1710 can be an imaging device (e.g., an X-ray machine) that provides images to the documentation service 1712 after the images are captured.

As described in detail herein, the transformative processing engine 202 can be configured to receive communications from many different systems, devices, and the like (e.g., the components 1710) and perform one or more operations on the communications. For example, the transformative processing engine 202 can store data, can transform and/or translate data, can direct data to other engines (e.g., the suggestion engine 1702) and/or entities outside the provider, and the like. The transformative processing engine 202 can provide processed data and/or raw data to the documentation service 1712.

The suggestion engine 1702 is shown in communication with the documentation service 1712. The suggestion engine 1702 accesses knowledge artifacts and based on other data, generates suggestions. The suggestion engine 1702 accesses the data in real-time or substantially real-time. Data includes real world conditions data, specific details about a dependent user (e.g., data associated with a record of the dependent user), and details about attention scenarios of the dependent user for which the suggestion engine 1702 will make the suggestions. For example, the suggestion engine 1702 may receive data in the form of output from a computerized treatment machine (e.g., one of the components 1710). The output may be associated with a dependent user who was receiving treatment by the computerized treatment machine. The suggestion engine 1702 accesses the output, which identifies the particular dependent user, and runs through a list of potentially-relevant knowledge artifacts that may assist the suggestion engine 1702 in making a suggestion to an authorized user who is authorized to attend to the particular dependent user. For example, the suggestion engine 1702 may determine that, based on a knowledge artifact (external, internal, or a combination) dealing with kidney failure, a particular drug may be helpful for the particular dependent user. This information (i.e., recommended drug) is then provided to the authorized user, who is one of the receiving users 1704, as a suggestion, with an option to automatically place an process action for the drug. In this manner, the contextual suggestions described may be based on the current data, knowledge artifacts, and output parameters and configuration settings (e.g., user-defined and machine-defined (e.g., learned) rules that define what output will be presented, how it will be presented, and other details about presentation) of certain components 1710.

The suggestion engine 1702 may interact using the active unified data layer 308 or the access management layer 310. In some examples, at least a portion of the interactions of the suggestion engine 1702 take place in the interface layer 316 and/or the application/device layer 320. In this manner, the suggestion engine 1702 may be configured to provide suggestions to the user interfaces 1706 via the interface layer 316 and/or the application/device layer 320. The user interfaces 1706 are examples of the user interfaces capable of generation by the interface engine 702 and may be accessed by the receiving users 1704 using applications running on user devices as described herein. The suggestion engine 1702 provides the suggestions to the user interfaces 1706 by sending the suggestions in accordance with an earlier subscription and/or by publishing the suggestion to a common location, which may be accessed by an application supporting the user interface 1706 (e.g., via one or more application programming interfaces (API) calls).

In some examples, the output from the suggestion engine 1702 is used by the documentation service 1712 as part of performing techniques relating to managing documentation as described herein. In some examples, functionality of the suggestion engine 1702 can be consolidated in the documentation service 1712 or functionality of the documentation service 1712 can be consolidated in the suggestion engine 1702. In any event, it should be understood, however, that the suggestion engine 1702 and the documentation service 1712 may, in some examples, provide similar information to similar users 1704 under similar conditions. In some examples, the workflows by which the output information is introduced to the users 1704 may be different. For example, the documentation service 1712 may provide a workspace that includes a set of graphical user interfaces for interacting with the documentation service 1712. The suggestion engine 1702 may provide its output information to a contextual user interface.

Turning now to the details of the documentation service 1712, the documentation service 1712 can include a communication engine 1714, a process action determination engine 1716, a documentation generation engine 1718, an execution engine 1720, and a documentation datastore 1722. Each of the engines 1714-1720 is configured to manage one or more sub-modules, components, engines, and/or services directed to examples disclosed herein. While these engines are illustrated in FIG. 17 and will be described as performing discrete tasks with reference to the flow charts, it is understood that FIG. 17 illustrates example configurations and other configurations performing other tasks and/or similar tasks as those described herein may be implemented according to the techniques described herein.

As introduced previously, the documentation datastore 1722 can include a process action database 1724, a documentation database 1726, a user data database 1728, and a record data database 1730. In some examples, at least a portion of the data stored in the documentation datastore 1722 can be stored in connection with the transformative processing engine 202. The databases in the datastore 1722 can be any suitable data structure configured to store information. For example, the databases can be on-disk databases, in-memory databases, relational databases, object-oriented databases, XML databases, and any other suitable data structure. In some examples, the documentation datastore 1722 is implemented in connection with the data store 508. For example, the process action database 1724, the documentation database 1726, the user data database 1728, and/or the record data database 1730 may be combined with or otherwise exist within the record data store 518, the general data store 520, the operational data store 522, the entity-based data store 524, and/or the streaming caching storage 526.

The process action database 1724 includes information about process actions that can be suggested by the process action determination engine 1716. For example, the process action database 1724 can include a table of potential process actions organized in any suitable manner. For example, the process actions can be organized according to an associated problem that may be present on an associated problem list. In some examples, process actions can be associated with other process actions. For example, sets of process actions that are typically ordered together can be associated such that if one process action is selected, the other process actions can be identified and it can be determined whether the other orders should also be selected. Associations between process actions may be particular to authorized users or groups of authorized users (e.g., grouped by facility, organization, specialty, geography, etc.), or may be generic to all authorized users. Associations may also be based on the substance of the process actions.

In some examples, the process action database 1724 is configured to store information about future process actions selected by professional users. For example, the process action database 1724 can function as a digital repository for storing future process actions. The future process actions can be stored in the digital repository at least until a professional user accepts, declines, alters, or otherwise interacts with the future process action. If the professional user accepts the future process action, an action will be performed. If the professional user, declines the future process action, the future process action will be removed from the digital repository. In any event, information about how the professional user interacts with the future process actions can be stored and used at a later time to improve suggested process actions for the professional user and other professional users.

The documentation database 1726 includes information about documentation that can be suggested by the documentation generation engine 1718. For example, the documentation database 1726 can include a table of pre-populated text items (e.g., words, text strings, numeric values, phrases, etc.). Each entry of a text item in the documentation database 1726 can be associated with one or process actions in the process action database 1724. Examples of text items can include alphanumeric text strings identifying any suitable aspect of documentation relating to the encounter. As described in detail herein, in some examples, text items from the documentation database 1726 can be tailored to a particular dependent user, to a class of dependent users to which the dependent user belongs, to a professional user, to a class of professional users to which the professional user belongs, to a facility at which the dependent user is being treated, to a geographic region in which the dependent user is being treated, and the like. This can include revising the text items to be more specific to any one or more of the characteristics identified above.

The user data database 1728 includes user information about professional user and dependent users. For example, for a professional user, the user information can include identifying information, demographic information, education information, work history information, specialty information, practice history information, and the like. For example, an entry in the user data database 1728 can identify the following information about a particular authorized user:

Name: Redd Wilson; age: 45; location: Barnesville, Va.; education: Bachelors of Science at University of Apples, Doctor of Medicine at the Best University; work history: Uptown hospital; specialty: internal medicine; practice history: description of previous diagnosis and associated orders.

The user information for dependent users and associated individuals can include identifying information, demographic information, historical record information, and the like. Using the user data database 1728, the documentation service 1712 can generate process actions and other suggestions that are particular to a professional user, particular for professional users similar to the professional user, particular to a dependent user, particular to dependent users similar to the dependent users, particular for a geographic area, particular for a time of year, and tailored in any other manner.

In some examples, the user information represents models for a particular dependent user, a group of dependent users, a particular professional user, or a group of professional users.

The record data database 1730 can be used to save electronic records associated with dependent users. For example, if the document service 1712 provides a workspace for inputting documentation about a dependent user, in some examples, the documentation is saved in the record data database 1730. In some examples, the record data database 1730 is accessed to identify a location of a user record of a dependent user that is saved at a different location (e.g., a different record data database 1730).

The communication engine 1714 is configured to generate one or more user interfaces (e.g., the user interfaces 1706). The user interfaces can be used by users (e.g., the users 1704) to interact with the documentation service 1712. In an illustrative example, the communication engine 1714 can provide a workspace by generating a user interface that includes a process action area (e.g., an order area) and a documentation area. In the process action area can be presented past, suggested, or scheduled process actions associated with a dependent user. In the documentation area can be presented documentation that describes encounters between the dependent user and certain professional users that are responsible for the dependent user. For example, a professional user may input text—a form of documentation—that describes conditions of a dependent user as observed by the professional user during an office visit, rounds, or other encounter between the dependent user and the professional user. The text can be included in (or on its own can be) a historical record associated with the dependent user's clinical record. In this manner, the documentation can describe conditions relating to the dependent user (e.g., diagnoses, treatment plans, health metrics, and the like). The information in the documentation can be objective data (e.g., structured data) and subjective data (e.g., unstructured data, free-form narratives, etc.). The professional user can use the documentation area to input documentation and/or interact with existing documentation relating to the dependent user.

The communication engine 1714 is also configured to enable communication between the users 1704 and the documentation service 1712. Such communication may be in the form of notifications pushed to the components 1710 or other devices such as user devices (e.g., mobile phones, laptops, etc.). In some examples, the communications from the documentation service 1712 may be presented within the workspace. For example, while the user 1704 interacts in the documentation area, updates can be made within the process action area (e.g., suggested process actions) and notifications about the suggested process actions can be presented. In some examples, the data analysis engine 1732 executes at the component 1710. For example, the language processing performed by the data analysis engine 1732 can be performed locally, the results of which can be shared with the documentation service 1712 for determination and presentation of process actions.

The process action determination engine 1716 is configured to process documentation (e.g., structured and unstructured data), which may include text data, voice data, output from a specialized component, and the like, in order to determine a set of process actions. In this manner, the process action determination engine 1716 can function in a manner similar to the suggestion engine 1702. In some examples, the documentation is input and/or accessed by the process action determination engine 1716 via the workspace (e.g., saved in documentation database 1726 of the documentation datastore 1722). In other examples, the process action determination engine 1716 analyzes documentation in an electronic user record that is saved using a separate service (e.g., by the transformative processing engine 202). The process action determination engine 1716 analyzes the documentation to identify process action indicators that can be indicative of a future process action (e.g., a process action that the professional user has described in the documentation or is likely to place given a description in the documentation), determines sets of process actions based on the process action indicators, and presents the sets of process actions to the professional user or other authorized user directly or places the sets of process actions in a digital repository (e.g., a process action cart). In this manner, the process action determination engine 1716 can include a data analysis engine 1732 including a structured data analysis engine and an unstructured data analysis engine. Thus, the process action determination engine 1716 can use text recognition techniques such as natural language processing to analyze documentation.

In some examples, the data analysis engine 1732 is configured to monitor, collect, receive, and otherwise process data (e.g., documentation) such that a process action for a dependent user can later be generated. In particular, the data analysis engine 1732 is configured to monitor, collect, receive, and otherwise process data is in a structured format and an unstructured format. In some examples, in order to derive meaningful information from the unstructured data, the data analysis engine 1732 uses one or more natural language processing techniques to analyze the unstructured data. Using these techniques, the data analysis engine 1732 identifies not only what words, symbols, and letters are included in the unstructured data, but also parses the unstructured data to identify meaning, tone, sentiment, humor, sarcasm, and other forms of speech present in the unstructured data. Examples of the unstructured data include: prose text written by an authorized user and included as an entry in a record of a dependent user or included in some other data structure, graphical depictions prepared by an authorized user and included as an entry in a record of the dependent user or included in some other data structure, prose text or graphical depictions prepared by a dependent user, a person related to the dependent user, and any other suitable unstructured data that can be analyzed by the data analysis engine 1732.

Thus, as described herein, the data analysis engine 1732 can perform one or more techniques to identify elements (e.g., letters, symbols, numbers, verbs, adjectives, nouns, punctuation, and other parts of speech) of spoken text and/or written text and characteristics of the spoken text and/or written text that may be relevant to their message (e.g., tone, meaning, sarcasm, feelings, inferences, impressions, attitude, outlook, positive/negative/other, and any other characteristic). These techniques include, for example, natural language processing (NLP) using machine learning, Hidden Markov models, Dynamic time warping (DTW), neural networks, deep neural networks and other deep learning models, and any other suitable technique for identifying elements and/or characteristics of spoken text and/or written text.

Depending on the technique, the data analysis engine 1732 includes or is configured to use a model to for analyzing documentation (e.g., spoken and/or written text) to identify words, phrases, symbols, meanings, etc. that can be interpreted as process action indicators. The process action indicators are indicative of a future process action. Each indicator may have a score assigned by the process action determination engine 1716, which may be influenced (e.g., increased or decreased) by other indicators being recognized and their respective scores.

The documentation generation engine 1718 is configured to analyze process actions, whether performed, suggested, or otherwise, and determine whether an associated user record (e.g., an electronic record) has adequate documentation to support the process actions. To this end, the documentation generation engine 1718 can include documentation rules associated with types, sets, groups, classes, and/or individual process actions. As documentation requirements may differ across providers, billing services, documentation laws (e.g., federal, state, and local), business practices, and the like, the documentation rules may account for these variations. For example, in order for an organization to be reimbursed for performing a particular test administered to a dependent user, the dependent user's electronic record must indicate certain vital signs within a range, a list of previous tests performed, and include a narrative prepared by a professional user that explains her subjective belief why the test was needed. The documentation rules associated with the this test may indicate each necessary item of information as a condition. The conditions can be weighted. For example, a condition relating to the presence of the dependent user's vital signs may be of greater weight than a condition relating to previous tests.

Once the documentation generation engine 1718 has analyzed the documentation in accordance with the documentation rules, it then suggests certain text and/or other documentation that should be added to the electronic record. The text and/or other documentation can be pulled from the documentation database 1726 in the documentation datastore 1722. The suggested items (e.g., text and/or documentation) can be included in a list and presented to the professional user, or added to a digital repository (e.g., a suggestion cart). The professional user can then select which items to add to the electronic record (e.g., by selecting suggested items or batches of items from the suggestion cart). Adding an item to the electronic record can include the professional user copying and pasting the text at a destination determined by the professional user. In some examples, the documentation generation engine 1718 can suggest a destination for the suggested item in the form of a text prompt or highlighting the area in the electronic record. In some examples, selection of a suggested item causes the suggested item to be automatically saved at an associated destination in the electronic record. In this manner, the professional user can save a substantial amount of time by auto-adding documentation to the electronic record.

The execution engine 1720 is configured to perform one or more actions relating to the execution of process actions selected by professional users (e.g., stored in a digital repository). In some examples, this can include placing a process action. To do so, a professional user can select a suggested process action or batch or related or unrelated process actions from the digital repository. Once selected, the execution engine 1720 can prepopulate at least a portion of the fields in the process action. Placing the process action can take place using typical methods (e.g., sending to the entity fulfilling the process action, printing and sending with a dependent user to take to the entity, and the like).

The execution engine 1720 is also configured to reconcile sets of process actions, documentation, and problem lists. In some examples, problem lists may be used within electronic records to list conditions of dependent users and plans for responding to the conditions. Problem lists typically identify the time of occurrence or identification and resolution of the condition. In this manner, the problem list may be a type of documentation that is particularly tied to not only a single process action, but to many process actions, a plan for responding to a condition, and the like. Thus, the execution engine 1720 can include reconciliation rules to evaluate process actions, documentation, problem lists, and any other suitable information. The reconciliation rules also include conditions for identifying inconsistencies, errors, and the like between the process actions, documentation, problem lists, and other information. These inconsistencies may be simple oversights or typographic errors, incomplete information (e.g., incomplete process actions), missing information, incorrect or incongruent information, incomplete suggestions, and the like. The execution engine 1720 generates a reconciliation item in the form of a suggestion for resolving the inconsistency or other error. These reconciliation items can be presented to a professional user and/or added to a digital repository for later review. The professional user can then access the reconciliation suggestions and determine whether to take one or more actions based on the suggested items.

The execution engine 1720 can also generate the suggested actions. Such actions can include any suitable action relating to problem lists, process actions, documentation, and/or support output. For example, such actions can include following up with a dependent user regarding results of a process action, revising an existing problem statement or creating a new problem statement that complies with one or more standards, adding documentation to an electronic record relating to a process action, populating fields of an incomplete process action with suggested information, and the like. Selection of a suggested item, may cause the execution engine 1720 to automatically execute the reconciliation item. In some examples, the professional user is provided with an opportunity to review the action before it is executed.

Figure 18:
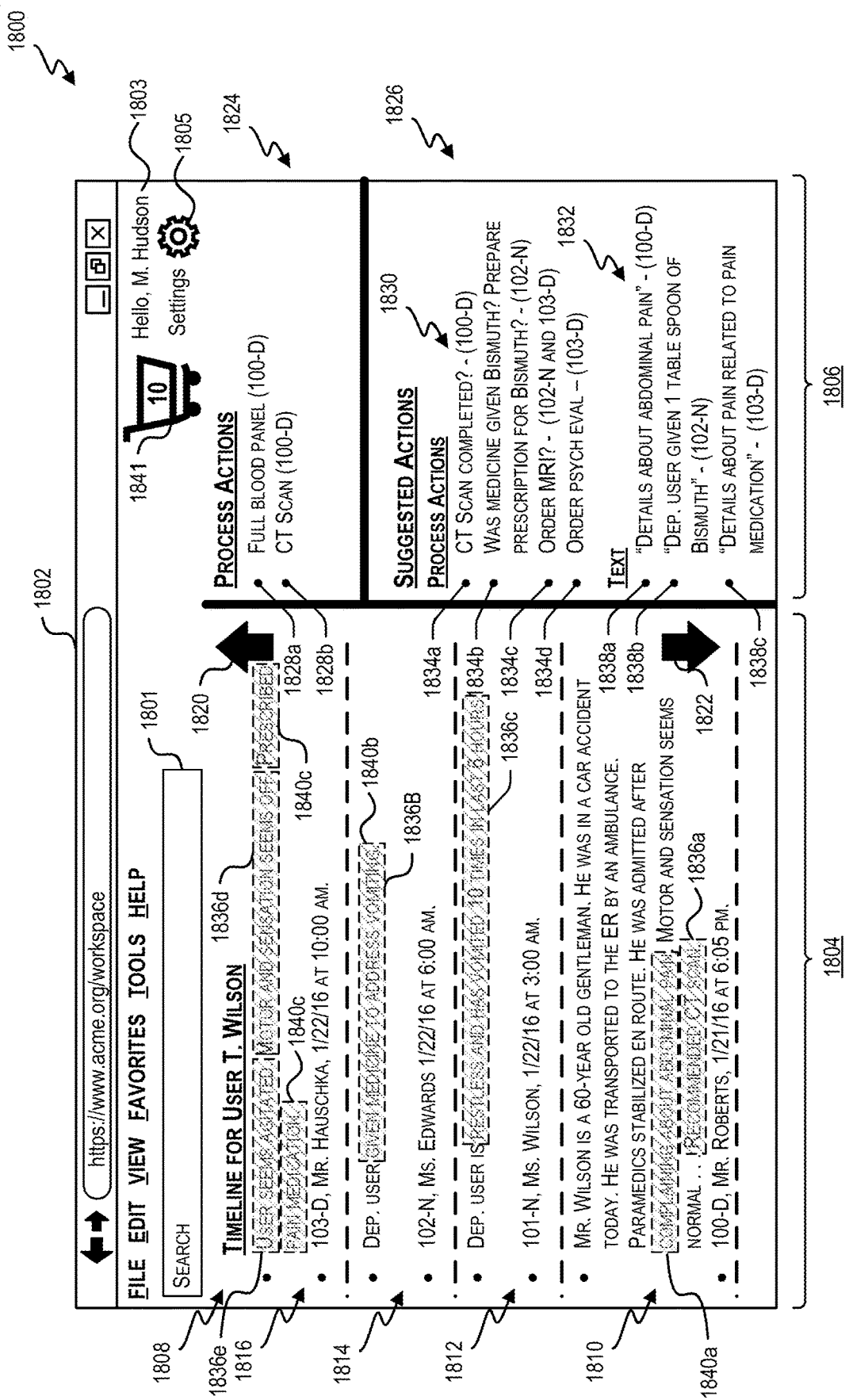
FIG. 18 is an example block diagram illustrating an example user interface in which techniques relating to determining process actions based on documentation as described herein may be implemented, according to at least one example.

FIG. 18 illustrates an example workspace user interface 1800 according to at least one example. The workspace user interface 1800 is an example of one of the user interfaces 1706. Thus, in this example, one or more engines of the documentation service 1712 (e.g., the communication engine 1714) can generate the workspace user interface 1800 (e.g., on a user device associated with one of the users 1704 and/or one of the components 1710). The workspace user interface 1800 is illustrated as a webpage 1802. Thus, in some examples, the workspace user interface 1800 is provided via web application over a network connection. In other examples, the workspace user interface 1800 is provided by an application installed on the user device that views the workspace user interface 1800. The workspace user interface 1800 includes a search bar 1801 for searching within a provider network, the Internet, any other network, or within a database, data structure, or the like. The workspace user interface 1800 also identifies Mr. Hudson 1803 as a professional user who has signed into the webpage 1802. Mr. Hudson 1803, or other user, may adjust the settings of how the webpage 1802 is configured and what information is presented by clicking on a settings icon 1805. Once Mr. Hudson 1803 adjusts the settings of the webpage 1802, the adjusted settings may be provided to the documentation service 1712 to consider when presenting information to Mr. Hudson 1803 via the webpage 1802. Mr. Hudson 1803 is currently viewing a part of an electronic record associated with dependent user, T. Wilson. In some examples, Mr. Hudson 1803 searched for T. Wilson using the search bar 1801, selected T. Wilson from a list of active dependent users, or otherwise was informed to view T. Wilson's electronic record.

The workspace user interface 1800 includes a documentation area 1804 and an process action area 1806. The documentation area 1804 includes a timeline 1808. The timeline 1808 includes a collection of note entries 1810-1816 corresponding to the dependent user, "T. Wilson." The note entries 1810-1816 are examples of documentation that has been inputted by one or more professional users. The timeline 1808 is organized with the most recent note entries at the top of the timeline 1808. The note entries 1810-1816 can also be organized, sorted, and/or filtered based on any other characteristic (whether included in the entry or in metadata associated with the entries) of the note entries 1810-1816. Using arrows 1820 and 1822, a user can scroll to show more recent note entries or older note entries, when such entries exist.

Each note entry 1810-1816 can include a description portion, a note identifier, a professional user identifier, and a timestamp. For example, the description portion describes the circumstances surrounding Mr. Wilson's visit to the ER, the note identifier ("100-D") uniquely identifies the note entry 1810, the professional user identifier ("Mr. Roberts") uniquely identifies the person who made the note entry 1810, and the timestamp ("1/21/16 at 6:05 pm") identifies a time when the note entry 1810 was saved. Corresponding information is shown for the other note entries 1812-1816. In some examples, the note entries 1810-1816 include any suitable information that describes the conditions of the dependent user, justifies process actions placed, and describes any other aspect of the dependent user.

In some examples, the note entries 1810-1816 may be entered in accordance with an existing procedure. For example, after Mr. Roberts admits the dependent user (e.g., the note entry 1810) after an ER visit, the next two note entries 1812, 1814 are made by other professional users while tending to the dependent user during the night/early morning, and the last note entry 1816 is made by Mr. Hauschka as part of conducting his rounds and checking on dependent users. In some examples, Mr. Hauschka may be a professional user associated with the facility where the dependent user is located or may be the dependent user's family professional. In any event, the note entries 1810-1816 may be entered by different individuals and describe different aspects of responding to current condition of the dependent user.

The process action area 1806 includes a process action area 1824 and a suggested action area 1826. The process action area 1824 includes placed process actions 1828a, 1828b. The placed process actions 1828a, 1828b are process actions that have been performed on or on behalf of T. Wilson. In this example, Mr. Hudson 1803 did not place the process action, but likely Mr. Roberts placed them. This may be because support for the placed process actions 1828a, 1828b can be found in note entry 1810 (100-D) made by Mr. Roberts.

The suggested action area 1826 includes suggested actions that can be taken by a professional user (e.g., Mr. Hudson 1803). Suggested actions can be generated by the process action determination engine 1716 of the documentation service 1712 based on information in the timeline 1808, information in the datastore 1722, and other suitable information that can be learned and/or is accessible to the documentation service 1712. For example, the process action determination engine 1716 can analyze the text included in the timeline 1808 using natural language processing techniques. In some examples, the same techniques are applied to a conventional electronic record of the dependent user (e.g., one organized in a manner that lacks the timeline 1808).

The suggested action area 1826 includes suggested process action list 1830 and suggested documentation list 1832. The suggested process action list 1830 can include one or more process actions 1834a-1834d. The process actions 1834a-1834d can be presented to Mr. Hudson 1803 in a manner that he can decide which of the process actions require follow up, should be processed, and or otherwise addressed based on the timeline 1808. For example, the process actions 1834a, 1834b correspond to process actions that have been placed. Mr. Hudson 1803 can review the process actions 1834a, 1834b to ensure that they were actually executed. The process actions 1834a, 1834b can be populated in the suggested process action list 1830 based on one or more process action indicators 1836a, 1836b. The process action indicators 1836 can be identified using one or more text recognition techniques (e.g., natural language processing techniques). For example, the process action 1834a ("CT Scan Completed?") can be based on text in the note entry 1810 that Mr. Roberts suggested a CT scan, i.e., the process action indicator 1836a. Similarly, the process action 1834b ("Was medicine given bismuth?") can be based on text in the note entry 1814 that Nurse Edwards gave medicine to address vomiting, i.e., the process action indicator 1836b. The process action 1834b can also include a suggested process action ("Prepare prescription for Bismuth?") that can also be based on the process action indicator 1836b.

The process actions 1834c, 1834d are suggested process actions that have been generated and populated into the suggested process action list 1830 based on one or more process action indicators 1836. For example, the process action 1834c ("Order MRI?") can be based on text in the note entry 1812 that the dependent user vomited numerous times during the evening, i.e., the process action indicator 1836c, and the text in the note entry 1816 that the dependent user's motor sensations seemed off, i.e., the process action indicator 1836d. The process action 1834d ("Order psych eval?") can be based on text in the note entry 1816 that the dependent user seemed agitated, i.e., the process action indicator 1836e. In some examples, the suggested process actions 1834c, 1834d are examples of decision support output generated by the suggestion engine 1702. The suggested process actions 1834 can be based on more process action indicators 1836 other than those discussed above. In some examples, the process action indicators 1836 can be structured data such as vital signs, other process action results, and the like. In some examples, a professional user can input process action indicators 1836 by inputting text in a particular manner that will be recognized as an needing an order. For example, "#" can be placed before type of medicine ("# Tylenol") in a note entry. This can function as a process action indicator 1836. The system can determine, based on # Tylenol, that a prescription for Tylenol should be suggested. Details about the order for Tylenol can be determined based on the dependent user T. Wilson (e.g., height and weight, age, allergies, other known medications, identified illnesses, etc.), based on Mr. Hudson 1803 (e.g., her prescription habits for Tylenol for dependent users like T. Wilson), and any other characteristic described herein.

The suggested documentation list 1832 can include one or more suggested text items 1838a-1838c that can be added to the note entries 1810-1816 to add adequate documentation to support the process actions 1834 and/or the process actions 1828. The suggested documentation list 1832 can be generated by the documentation generation engine 1718. Thus, the suggested documentation list 1832 can include suggested text items 1838 for prepared process actions, placed process actions, and suggested process actions. The one or more suggested text items 1838 can be based at least in part on one or more documentation indicators 1840, or one or more process actions 1828 and/or 1834. For example, the suggested text item 1838a ("Details about abdominal pain") can be based on text in the note entry 1810 that the dependent user complained about abdominal pain, i.e., the documentation indicator 1840a. In some examples, it may be beneficial to add the suggested text item 1838a to the note entry 1810 in order to justify the CT scan that was ordered by the note entry 1810. The suggested text item 1838a may be necessary for insurance billing purposes and for any other suitable purpose described herein. In some examples, the details about the abdominal pain may include specific details that can be input directly into the note entry 1810.

The suggested text item 1838b ("Dependent user given 1 table spoon of bismuth") can be based on text in the note entry 1814 that the dependent user was given medicine to address vomiting, i.e., the documentation indicator 1840b. In some examples, it may be beneficial to add the suggested text item 1838b to the note entry 1814 to add additional description about the medicine administered. The suggested text item 1838b can include a suggested amount based on historical data about the particular professional user that administered the medicine, professional users like the particular professional user, historical data about the dependent user, or historical data about dependent users like the dependent user, T. Wilson. In some examples, Mr. Hudson 1803 can select to add the suggested text item 1838b and the particular user who completed the note entry 1814 (e.g., Ms. Edwards) can verify that the suggested text item 1838b is accurate.

The suggested text item 1838c ("Details about pain related to pain medication") can be based on text in the note entry 1816 that the dependent user was prescribed pain medication, i.e., the documentation indicator 1840c. For example, the note entry 1816 that the dependent user was prescribed pain medication may require documentation that supports the prescription. For example, it is not entirely clear from the timeline 1808 why the dependent user was prescribed pain medication. Thus, the suggested text item 1838c can include actual text that can be added to the note entry 1816 (or other note entries 1810-1014) to describe the pain associated with the pain medication. In some examples, the documentation generation engine 1718 can scan the timeline to determine the content of the suggested text items 1838. For example, the pain medication prescribed in the note entry 1816 could be based on the abdominal pain complained of by the dependent user in the note entry 1810. Thus, the suggested text item 1838c can be based on the note entry 1816. The suggested text item 1838c can also include a likely amount and/or a suggested amount for the dependent user T. Wilson based on characteristics of the dependent user (e.g., allergies, height weight, other medications, etc.) and characteristics of Mr. Hudson and/or Mr. Hauschka (e.g., prescribing habits, etc.).

The workspace user interface 1800 can include a representation of a digital repository 1841. The representation of the digital repository 1841 represents an example digital shopping cart or other digital repository for storing information. As described herein, the digital repository can function as a repository for suggested process actions. The representation of the digital repository 1841 is a cart graphic with a numerical indicator. The numerical indicator can correspond to the number of outstanding suggested process actions for resolution by Mr. Hudson 1803. In some examples, once Mr. Hudson 1803 selects one of the suggested process actions from the suggestion action area 1826, the selected suggested process action can be added to the digital repository represented by 1841. In some examples, the suggested process actions are added to the digital repository represented by 1841 as Mr. Hudson 1803 prepares a note entry in the documentation area 1804. In some examples, Mr. Hudson 1803 can access the digital repository represented by 1841 and further interact with the added process actions. In some examples, the process actions in the digital repository represented by 1841 can include process actions for the dependent user T. Wilson and for other dependent users for whom Mr. Hudson 1803 is responsible. In some examples, the process actions in the digital repository represented by 1841 can be grouped into sets and subsets based on any suitable parameter (e.g., dependent user, type of action (e.g., process action or documentation text), sub-type of each action (e.g., type of process action or type of documentation text), criticality, time for execution, etc.). In some examples, Mr. Hudson 1803 can authorize and a group of process actions to be executed as a batch. In some examples, the group of process actions can be executed in parallel or in series.

Figure 19:
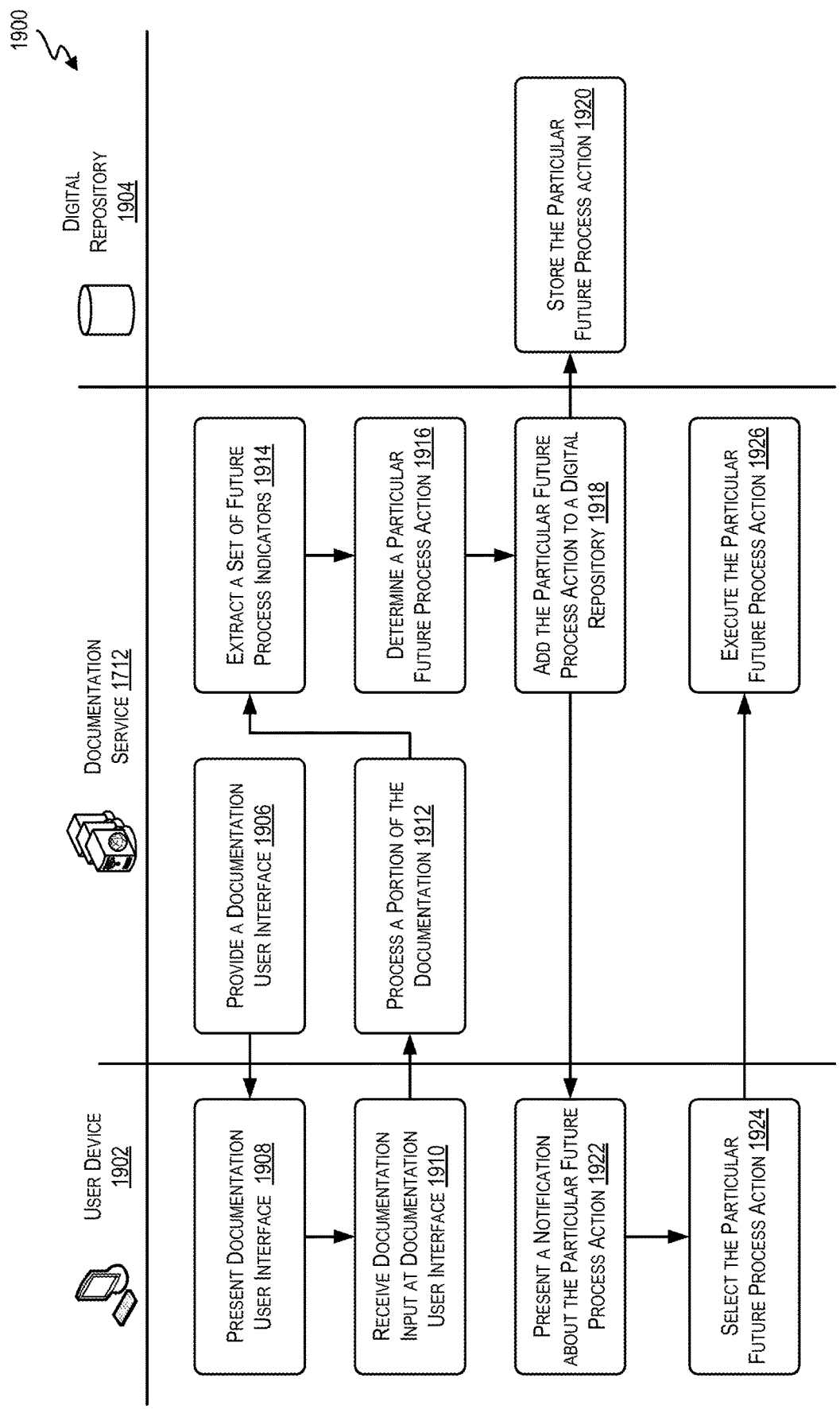
FIG. 19 is a flow diagram depicting example acts for implementing techniques relating to determining process actions based on documentation as described herein, according to at least one example.
Figure 20:
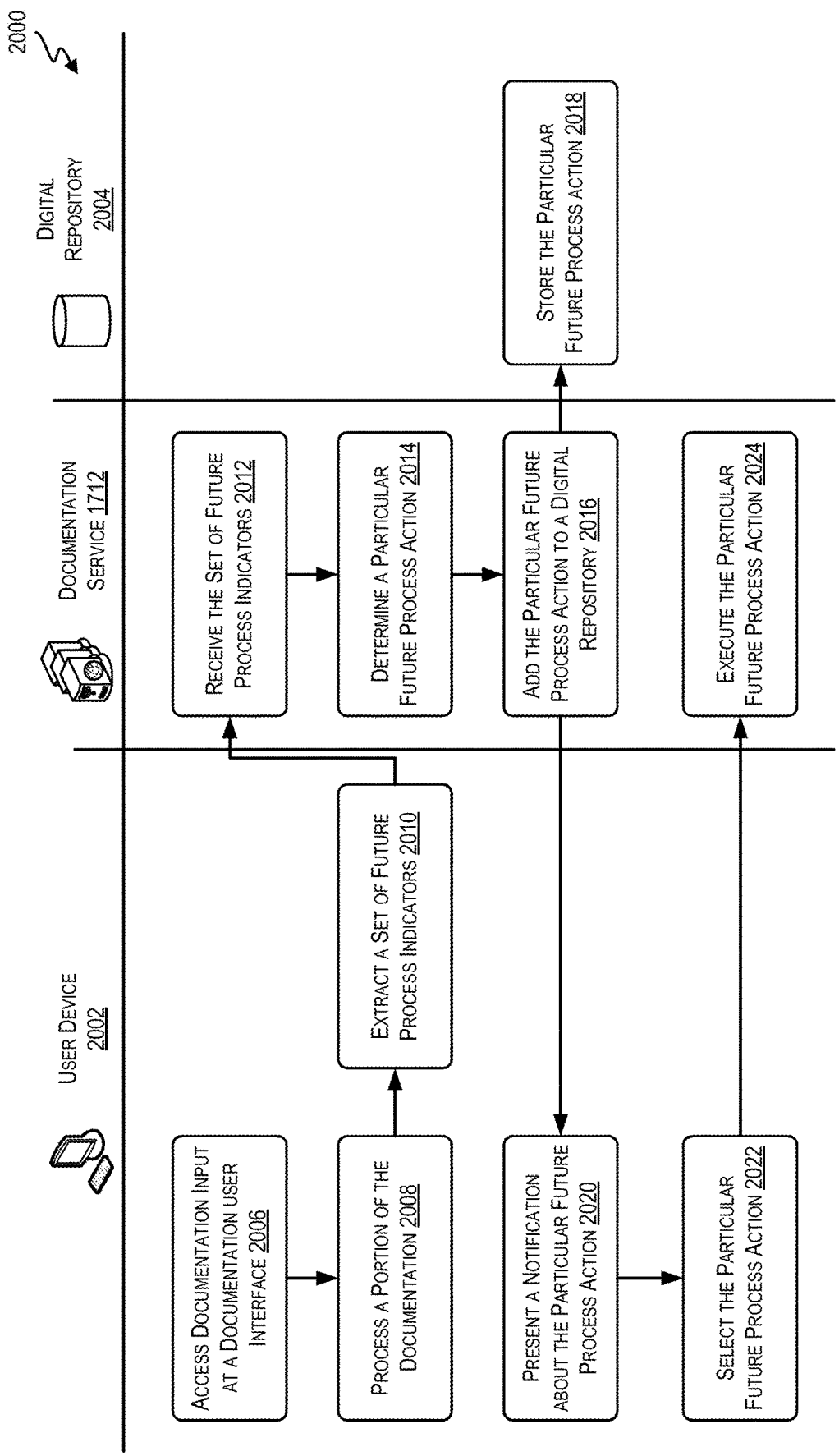
FIG. 20 is a flow diagram depicting example acts for implementing techniques relating to determining process actions based on documentation as described herein, according to at least one example.
Figure 21:
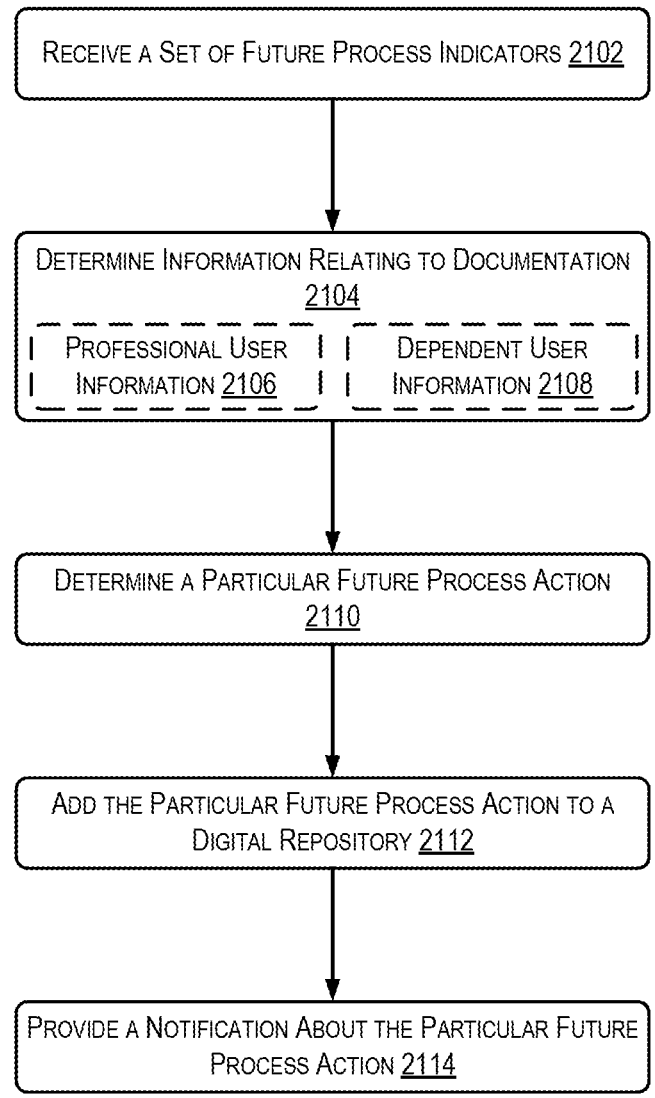
FIG. 21 is a flow diagram depicting example acts for implementing techniques relating to determining process actions based on documentation as described herein, according to at least one example.

FIGS. 19, 20, and 21 illustrate example flow diagrams showing respective processes 1900, 2000, and 2100 as described herein. These processes 1900, 2000, and 2100 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium (e.g., computer storage devices), for example, in the form of a computer program comprising a plurality of instructions executable by one or more processors. The computer-readable storage medium is non-transitory.

FIG. 19 depicts the process 1900 including example acts or techniques relating to determining future process actions based on documentation, according to at least one example.

The process 1900 of FIG. 19 may be performed by a user device 1902, the documentation service 1712, and a digital repository 1904. The user device 1902 is an example of one of the components 1710. The digital repository 1904 is an example of the process action database 1724.

The process 1900 begins at 1906 by providing a documentation user interface. In some examples, providing the documentation user interface is performed by the documentation service 1712.

At 1908, the process 1900 presents the documentation user interface. In some examples, presenting the documentation use interface is performed by the user device 1902. In some examples, the process 1900 further includes enabling a user to use the documentation use interface to input documentation relating to an encounter with a dependent user. In some examples, the documentation includes unstructured data and/or structured data.

At 1910, the process 1900 receives documentation input at the documentation user interface. In some examples, receiving the documentation input at the documentation user interface is performed by the user device 1902. In some examples, the process 1900 further includes accessing a portion of the documentation. This may be performed by the documentation service 1712.

At 1912, the process 1900 processes the portion of the documentation. In some examples, processing the portion of the documentation is performed by the documentation service 1712. The documentation service 1712 can receive the portion of the documentation from the user device 1902. This may be because the portion of the documentation was input by the user at the documentation user interface of the user device 1902. In some examples, processing the portion of the documentation includes using a natural language processing techniques to process written text and/or spoken text in the portion of the documentation.

At 1914, the process 1900 extracts a set of future process indicators. In some examples, extracting the set of future process indicators is performed by the documentation service 1712. In some examples, the future process indicators are extracted from the documentation using a natural language processing technique. The set of future process indicators are indicative of one or more of a plurality of future process actions performable with respect to dependent users. In some examples, the natural language processing technique is performed at least while the user is inputting the documentation at the documentation user interface. Thus, the natural language processing technique can be performed simultaneously while the user inputs documentation.

At 1916, the process 1900 determines a particular process action. In some examples, determining the particular process action is performed by the documentation service 1712. The particular process action may be determined based on the set of future process indicators.

In some examples, the particular future process action may be performed with respect to the dependent user. The future process action can be described by the user in the portion of the documentation in order to respond to a current condition of the dependent user identified during the encounter. For example, if the user were responsible for the dependent user, the dependent user may visit the user and the user may write a description of the visit (e.g., the encounter).

In some examples, the process 1900 further includes determining professional user information associated with the user who contributed at least the portion of the documentation. The professional user information is representative of at least one of a first characteristic of the user or a second characteristic shared by a group of users that is similar to the user. In some examples, determining the particular future process action is further based at least in part on the professional user information.

In some examples, the process 1900 further includes determining dependent user information associated with the dependent user. The dependent user information is representative of at least one of a third characteristic of the dependent user or a fourth characteristic shared by a group of dependent users that is similar to the dependent user. In some examples, determining the particular future process action is further based at least in part on the dependent user information.

At 1918, the process 1900 adds the particular future process action to a digital repository. In some examples, adding the particular future process action is performed by the documentation service 1712. The digital repository may include other future process actions.

In some examples, determining the particular future process action includes determining a second future process action that is related to the particular future process action. The process 1900, in some examples, further includes adding the second future process action to the digital repository of future process actions.

At 1920, the process 1900 stores the particular future process action. In some examples, storing the particular future process action is performed by the digital repository 1904. Thus, the digital repository 1904 can store the particular future process action.

At 1922, the process 1900 presents a notification about the particular future process action. In some examples, presenting the notification is performed by the user device 1902. In some examples, the documentation service 1712 provides the notification for presentation at the user device 1902. The notification may indicate that the particular future process action is available in the digital repository for review by the user (e.g., the user of the user device 1902).

At 1924, the process 1900 selects the particular future process action. In some examples, selecting the particular future process action is performed by user device 1902. For example, a user of the user device 1902 can use the user device 1902 to select the particular future process action from a set of future process actions. In some examples, selecting the particular future process action includes the documentation service 1712 receiving information indicating the selection.

At 1926, the process 1900 executes the particular future process action. In some examples, executing the particular future process action is performed by the documentation service 1712. Executing the particular future process action can include sending the particular process action to an entity or other user for execution. In some examples, executing the particular process action can include populating one or more fields of a document that can be provided to a different user to instruct the different user to perform the particular future process action.

FIG. 20 depicts the process 2000 including example acts or techniques relating to determining future process actions based on documentation, according to at least one example. The process 2000 of FIG. 20 may be performed by a user device 2002, the documentation service 1712, and a digital repository 2004. The user device 2002 is an example of one of the components 1710. The digital repository 2004 is an example of the process action database 1724.

The process 2000 begins at 2006 by accessing documentation input at a documentation user interface. In some examples, accessing the documentation is performed by the user device 2002. For example, the user device 2002 may provide the documentation user interface at which the documentation is entered. In some examples, providing the documentation user interface is performed by the documentation service 1712.

At 2008, the process 2000 processes a portion of the documentation. In some examples, processing the portion of the documentation is performed by the user device 2002. Processing the portion of the documentation includes processing using a natural language processing technique. In some examples, processing can be performed during a time period or after the time period in which the documentation is input at the documentation user interface. In some examples, the documentation describes an encounter between a user and a dependent user. The documentation can include unstructured data that is input by the user at a documentation user interface during the time period. In some examples, a particular future process action can be performed with respect to the dependent user. The future process action is described by the user in the portion of the documentation in order to respond to a current condition of the dependent user identified during the encounter.

At 2010, the process 2000 extracts the set of future process indicators. In some examples, extracting the set of future process indicators is performed by the user device 2002. The set of future process indicators can be extracted, using a natural language processing technique, from the portion of the documentation. In some examples, the natural language processing technique is performed at least while the user is inputting the documentation at the documentation user interface.

At 2012, the process 2000 receives the set of future process indicators. In some examples, receiving the set of future process indicators is performed by the user device 2002. The set of future process indicators can be indicative of one or more of a plurality of future process actions performable with respect to dependent users.

At 2014, the process 2000 determines a particular future process action. In some examples, determining the particular future process action is performed by the documentation service 1712. In some examples, the set of future process indicators is determined based on the set of future process indicators.

In some examples, the process 2000 further includes determining professional user information associated with the user who contributed to at least the portion of the documentation. The professional user information can be representative of at least one of a first characteristic of the user or a second characteristic shared by a group of users that is similar to the user. In this example, determining the particular future process action is further based at least in part on the professional user information.

In some examples, the process 2000 further includes determining dependent user information associated with the dependent user. The dependent user information can be representative of at least one of a third characteristic of the dependent user or a fourth characteristic shared by a group of dependent users that is similar to the dependent user. In this example, determining the particular future process action is further based at least in part on the dependent user information.

At 2016, the process 2000 adds the particular future process action to a digital repository. In some examples, adding the particular future process action is performed by the documentation service 1712. The digital repository can be a digital repository of future process actions.

At 2018, the process 2000 stores the particular future process action. In some examples, storing the particular future process action is performed by the digital repository 2004.

At 2020, the process 2000 presents a notification about the particular future process action. In some examples, presenting the notification is performed by the user device 2002. The notification. In some examples, the notification may indicate that the particular future process action is available in the digital repository for review by the user (e.g., the user of the user device 2002).

At 2022, the process 2000 selects the particular future process action. In some examples, selecting the particular future process action is performed by the user device 2002 (e.g., by a user using the user device 2002).

In some examples, the process 2000 further includes receiving information indicating selection of the particular future process action by the user. The documentation service 1712 can receive the selection. In some examples, receiving the information indicating selection of the particular future process action includes receiving a relevance rating from the user of the particular future process action with respect to the documentation. In this example, the relevance rating is used as feedback for a natural language processing model used when the natural language processing technique is performed.

At 2024, the process 2000 executes the particular future process action. In some examples, executing the particular future process action is performed by the documentation service 1712. In some examples, executing the particular future process action includes causing the particular future process action to be sent to a different user or an entity for performance.

FIG. 21 depicts the process 2100 including example acts or techniques relating to determining future process actions based on documentation, according to at least one example. The process 2100 of FIG. 21 may be performed by the documentation service 1712.

The process 2100 begins at 2102 by receiving a set of future process indicators. The set of future process indicators is indicative of one or more of a plurality of future process actions performable with respect to dependent users. The set of future process indicators can be extracted from documentation using a natural language processing technique. In some examples, the documentation is prepared by a user to describe an encounter between the user and a dependent user. In some examples, the natural language processing technique is performed at least while the user is preparing the documentation.

At 2104, the process 2100 determines information relating to documentation. In some examples, the information includes professional user information 2106 associated with the user who contributed at least a portion of the documentation. The professional user information 2106 is representative of at least one of a first characteristic of the user or a second characteristic shared by a group of users that is similar to the user. In some examples, the information includes dependent user information 2108 associated with the dependent user. The dependent user information 2108 is representative of at least one of a third characteristic of the dependent user or a fourth characteristic shared by a group of dependent users that is similar to the dependent user. In some examples, determining the professional user information and/or the dependent user information is based on accessing one or more databases that include information for a plurality of professional users and/or a plurality of dependent users.

At 2110, the process 2100 determines a particular future process action. In some examples, the future process action can be performed with respect to the dependent user. In some examples, determining the particular future process action is based on the set of future process indicators, the professional user information, and/or the dependent user information. In some examples, the particular future process action is described by the user in the portion of the documentation in order to respond to a current condition of the dependent user that was identified during the encounter.

At 2112, the process 2100 adds the particular future process action to a digital repository. In some examples, the digital repository can be a repository of future process actions. The repository is a location where the user can go to review future process actions and select those that should be executed.

At 2114, the process 2100 provides a notification about the particular future process action. In some examples, the notification indicates that the particular future process action is available in the digital repository for review by the user (e.g., as numerical icon on a graphical chart).

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps, and means described above may be done in various ways. For example, these techniques, blocks, steps, and means may be implemented in hardware, software, or a combination thereof. For a hardware implementation, the processing units may be implemented within one or more application specific integrated circuits (Asics), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, and/or various other storage mediums capable of storing that contain or carry instruction (s) and/or data.

While the principles of the disclosure have been described above in connection with specific apparatuses and methods, it is to be clearly understood that this description is made only by way of example and not as limitation on the scope of the disclosure.

What is claimed:

1. A system comprising:
 a communication engine that:
  facilitates one or more user interfaces provided via one or more user devices; and
  processes input received via at least one user interface of the one or more user interfaces, the input corresponding to medical documentation relating to an interaction of a medical professional with a patient, where the medical documentation is gathered at least in part by permitting the medical professional to use the user interface to input at least part of the medical documentation at a documentation area;
 a process engine that:
  accesses first data corresponding to the medical documentation, the first data comprising unstructured data;
  processes the first data using a natural language processing technique to extract a set of one or more medical process indicators from the first data, the set of one or more medical process indicators indicative of one or more process actions that are performable with respect to patients, where the processing comprises analyzing the medical documentation at least partially by parsing subjective data corresponding to the unstructured data to identify one or more of meaning, tone, humor, and/or sarcasm in the subjective data;
compute a score for each medical process indicator of the set of one or more medical process indicators, select one or more knowledge artifacts based on the set of one or more medical process indicators, and determine, based on the one or more knowledge artifacts and the scores for the medical process indicators of the set of one or more medical process indicators, a particular process action to be performed with respect to the patient, the particular process action being described in the first data in order to respond to a current condition of the patient; and
adds an indicator of the particular process action to a digital repository storing indicia of process actions; and
the communication engine causing provisioning of a notification for presentation via at least one user device of the one or more user devices indicating the particular process action performable with respect to the patient.

2. The system of claim 1, wherein the at least one user interface corresponds to a documentation user interface that comprises a documentation area and an order area.

3. The system of claim 2, where:
the documentation area defines an area configured for input of note entries that describe one or more interactions comprising the interaction of the medical professional with the patient, and
the order area defines an area configured for presenting notifications about future orders that are automatically and contemporaneously suggested based on the note entries.

4. The system of claim 3, further configured to:
access an output from a computerized treatment machine, the output being associated with treatment with respect to the patient and being in an unstructured format;
where the unstructured data corresponds to the medical documentation input via the documentation user interface and the output from the computerized treatment machine.

5. The system of claim 4, where the determining the particular process action is determined based on the output from the computerized treatment machine.

6. A method comprising:
facilitating one or more user interfaces provided via one or more user devices;
processing input received via at least one user interface of the one or more user interfaces, the input corresponding to medical documentation relating to an interaction of a medical professional with patient, where the medical documentation is gathered at least in part by permitting the medical professional to use the user interface to input at least part of the medical documentation at a documentation area;
accessing first data corresponding to the medical documentation, the first data comprising unstructured data;
processing the first data using a natural language processing technique to extract a set of one or more medical process indicators from the first data, the set of one or more medical process indicators indicative of one or more process actions that are performable with respect to patients, where the processing comprises analyzing the medical documentation at least partially by parsing subjective data corresponding to the unstructured data to identify one or more of meaning, tone, humor, and/or sarcasm in the subjective data;
computing a score for each medical process indicator of the set of one or more medical process indicators, select one or more knowledge artifacts based on the set of one or more medical process indicators, and determining, based on the one or more knowledge artifacts and the scores for the medical process indicators of the set of one or more medical process indicators, a particular process action to be performed with respect to the patient, the particular process action being described in the first data in order to respond to a current condition of the patient;
adding an indicator of the particular process action to a digital repository storing indicia of process actions; and
causing provisioning of a notification for presentation via at least one user device of the one or more user devices indicating the particular process action performable with respect to the patient.

7. The method of claim 6, wherein the at least one user interface corresponds to a documentation user interface that comprises a documentation area and an order area.

8. The method of claim 7, where:
the documentation area defines an area configured for input of note entries that describe one or more interactions comprising the interaction of the medical professional with the patient, and
the order area defines an area configured for presenting notifications about future orders that are automatically and contemporaneously suggested based on the note entries.

9. The method of claim 8, further comprising:
accessing an output from a computerized treatment machine, the output being associated with treatment with respect to the patient and being in an unstructured format;
where the unstructured data corresponds to the medical documentation input via the documentation user interface and the output from the computerized treatment machine.

10. The method of claim 9, where the determining the particular process action is determined based on the output from the computerized treatment machine.

11. One or more non-transitory, computer-readable storage devices for storing computer-executable instructions that, when executed by one or more computer systems, configure the one or more computer systems to perform operations comprising:
facilitating one or more user interfaces provided via one or more user devices;
processing input received via at least one user interface of the one or more user interfaces, the input corresponding to medical documentation relating to an interaction of a medical professional with patient, where the medical documentation is gathered at least in part by permitting the medical professional to use the user interface to input at least part of the medical documentation at a documentation area;
accessing first data corresponding to the medical documentation, the first data comprising unstructured data;
processing the first data using a natural language processing technique to extract a set of one or more medical process indicators from the first data, the set of one or more medical process indicators indicative of one or more process actions that are performable with respect to patients, where the processing comprises analyzing the medical documentation at least partially by parsing subjective data corresponding to the unstructured data to identify one or more of meaning, tone, humor, and/or sarcasm in the subjective data;

computing a score for each medical process indicator of the set of one or more medical process indicators, select one or more knowledge artifacts based on the set of one or more medical process indicators, and determining, based on the one or more knowledge artifacts and the scores for the medical process indicators of the set of one or more medical process indicators, a particular process action to be performed with respect to the patient, the particular process action being described in the first data in order to respond to a current condition of the patient;

adding an indicator of the particular process action to a digital repository storing indicia of process actions; and causing provisioning of a notification for presentation via at least one user device of the one or more user devices indicating the particular process action performable with respect to the patient.

12. The one or more non-transitory, computer-readable storage devices of claim 11, wherein the at least one user interface corresponds to a documentation user interface that comprises a documentation area and an order area.

13. The one or more non-transitory, computer-readable storage devices of claim 12, where:

the documentation area defines an area configured for input of note entries that describe one or more interactions comprising the interaction of the medical professional with the patient, and the order area defines an area configured for presenting notifications about future orders that are automatically and contemporaneously suggested based on the note entries.

14. The one or more non-transitory, computer-readable storage devices of claim 13, the operations further comprising: accessing an output from a computerized treatment machine, the output being associated with treatment with respect to the patient and being in an unstructured format; where the unstructured data corresponds to the medical documentation input via the documentation user interface and the output from the computerized treatment machine.

15. The one or more non-transitory, computer-readable storage devices of claim 14, where the determining the particular process action is determined based on the output from the computerized treatment machine.

* * * * *